(12) United States Patent
Saarinen et al.

(10) Patent No.: US 8,313,912 B2
(45) Date of Patent: Nov. 20, 2012

(54) CANCER SPECIFIC OLIGOSACCHARIDE SEQUENCES AND USE THEREOF

(75) Inventors: Juhani Saarinen, Helsinki (FI); Jari Helin, Vantaa (FI); Tero Satomaa, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 463 days.

(21) Appl. No.: 10/486,714

(22) PCT Filed: Aug. 16, 2002

(86) PCT No.: PCT/FI02/00674
§ 371 (c)(1),
(2), (4) Date: Mar. 12, 2004

(87) PCT Pub. No.: WO03/016464
PCT Pub. Date: Feb. 27, 2003

(65) Prior Publication Data
US 2004/0253651 A1    Dec. 16, 2004

(30) Foreign Application Priority Data
Aug. 17, 2001   (FI) ................................ 20011664

(51) Int. Cl.
*G01N 33/53*   (2006.01)
*G01N 33/574*   (2006.01)

(52) U.S. Cl. ............................. 435/7.1; 435/7.23
(58) Field of Classification Search ............. 435/7.1, 435/7.21, 7.23, 7.91; 424/133.1, 174.1
See application file for complete search history.

(56) References Cited

U.S. PATENT DOCUMENTS

| | | | |
|---|---|---|---|
| 4,455,380 A * | 6/1984 | Adachi | 436/504 |
| 4,904,596 A | 2/1990 | Hakomori | |
| 5,660,834 A | 8/1997 | Kjeldsen et al. | |
| 6,187,754 B1 | 2/2001 | Oehrlein | |
| 6,261,788 B1 * | 7/2001 | Cummings et al. | 435/7.22 |
| 2006/0019256 A1 * | 1/2006 | Clarke et al. | 435/6 |

FOREIGN PATENT DOCUMENTS

| | | |
|---|---|---|
| EP | 0 565 241 A1 | 10/1993 |
| EP | 0565241 A1 * | 12/1993 |
| EP | 0 919 563 A2 | 6/1999 |
| WO | WO 93/17033 A1 | 9/1993 |
| WO | WO 00/17654 A1 | 3/2000 |
| WO | WO 02/077649 A1 | 10/2002 |

OTHER PUBLICATIONS

Kudryashov et al., Cancer Immunol Immunother,vol. 45, p. 281-286, 1998.*
Saarinen et al. Eur. J. Biochemistry 1999; 259: 829-840.*
Do et al. Glycobiology 1997; 7: 183-194.*
Goelz et al. J. Bio. Chem. 1994; 269: 1033-1040.*
Gawlitzek et al. J. Biotechnology 1995; 42: 117-131).*
Muzert et al. (Biotechnol. Prog. 1996; 12: 559-563).*
Yan et al. (Glycoconjugate Journal 1997; 14: 45-55).*
Yan et al. (Glycoconjugate Journal 1997; 14: 45-55, of record).*
Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-1802).*
Zips et al (In vivo, 2005, 19:1-7).*
Gura (Science, 1997, 278:1041-1042).*
Kaiser (Science, 2006, 313, 1370).*
Nyame et al., Experimental Parasitology, vol. 96, 2000, A. pp. 202-212.
Saarinen et al., Eur. J. Biochem., vol. 259, 1999, pp. 829-840.
Yamamoto et al., Biochemistry, vol. 33, 1994, pp. 8159-8166.
Shipova et al., Carbohydrates Letters, vol. 4, No. 2, 2001, pp. 85-90.
Young et al., J. Exp. Med., vol. 150, 1979 pp. 1008-1019.
Baisch et al., Bioorganic & Medicinal Chemistry Letters, vol. 8, 1998 pp. 751-754.
Sala et al., Carbohydrate Research, vol. 306, 1998 pp. 127-136.
Palcic, Current Opinion in Biotechnology, vol. 10, 1999, pp. 616-624.
Eijnden et al., Biochemical Society transactions, vol. 23, 1995, pp. 175-179.
A.A. Bergwerff et al.; FEBS 13224; vol. 334, No. 1; pp. 133-138; Nov. 1993.
A. Dell et al.; The Journal of Biological Chemistry; vol. 270, No. 41; pp. 24116-24126; Oct. 13, 1995.
A.J. Jaques et al.; Biochem. J.; 316; pp. 427-437; 1996.
S.M. Manzella et al.; The Journal of Biological Chemistry; vol. 272; No. 8; pp. 4775-4782; Feb. 21, 1997.
K-Y Do et al.; Glycobiology; 7(2); Mar. 1997.
B.W. Grinnell et al.; Glycobiology; 4(2); Apr. 1994.
R.K. Jain et al.; Glycobiology; 8(7); Jul. 1998.
D.H. Van Den Eijnden et al.; Biochem. Soc. Trans.; 25(3); Aug. 1997.

* cited by examiner

*Primary Examiner* — Peter J Reddig
*Assistant Examiner* — Yan Xiao
(74) *Attorney, Agent, or Firm* — Birch Stewart Kolasch & Birch, LLP

(57) ABSTRACT

The invention concerns a method for diagnosing cancer in a biological sample by determining the presence of a LacdiNAc oligosaccharide sequence. The invention can be used for diagnostic agents, pharmaceutical compositions, cancer vaccines, and antigenic carbohydrate substances. The presence of cancer and malignancies is determined by contacting the biological sample with a reagent that binds to the oligosaccharide sequence. This same method can also be used in the treatment of cancer and malignancies.

20 Claims, 15 Drawing Sheets

CANCER SPECIFIC OLIGOSACCHARIDE SEQUENCES AND USE THEREOF

FIELD OF THE INVENTION

The present invention relates to oligosaccharide sequences, which are specifically expressed by certain cancer cells, tumours and other malignant tissues. The present invention describes methods to detect cancer specific oligosaccharide sequences as well as methods for the production of reagents binding to said oligosaccharide sequences. The invention is also directed to the use of said oligosaccharide sequences and reagents binding to them for the diagnostics of cancer and malignancies. Furthermore, the invention is directed to the use of said oligosaccharide sequences and reagents binding to them for the treatment of cancer and malignancies.

BACKGROUND OF THE INVENTION

Various cancer cells or tissues express oligosaccharide sequences which are different from the non-malignant glycosylation of the same cell or tissue type. Examples of the known or speculated cancer associated oligosaccharide structures include: glycolipid structures such as globo-H (Fucα2Galβ3GalNAcβ3Galα4LacβCer), ganliosides: GM1 Galβ3GalNAcβ4(NeuNAcα3)LacβCer, or GD2 GalNAcβ4 (NeuNAcα8NeuNAcα3)LacβCer; Lewis-type fucosylated structures such as Lewis a and x Galβ3/4(Fucα4/3)GlcNAc, Lewis y Fucα2Galβ4(Fucα3)GlcNAc, sialyl-Lewis x NeuNAcα3Galβ4(Fucα3)GlcNAc, and some combinations of these on polylactosamine chains; O-glycan core structures such as T-antigen Galβ3GalNAcαSer/Thr-Protein, Tn-antigen GalNAcαSer/Thr-Protein or sialyl Tn-antigen NeuNAcα6GalNAcαSer/Thr-Protein. Presence of non-human structures such as N-glycolyl-neuraminic acid in cancers has also been indicated. Association and specificity of oligosaccharide structures with regard to cancers have been well established only in few cases, some of the structures are present in normal cells and tissues and are possibly only more concentrated in cancers. However, absolute cancer specificity is probably not always needed for therapeutic applications.

LacdiNAc (GalNAcβ4GlcNAc)-type glycosylations have not been found to be commonly present on human tissues. However, LacdiNAc-type saccharide sequences have been reported from many non-human animals, bovine glycoproteins, human glycoprotein hormones (Manzella et al., 1997) and human glycodelin protein, reviewed in van den Eijnden et al. (1997). Generally the structure seem to be associated with invertebrate animals and early development. Several LacdiNAc variants has been reported from proteins expressed in human embryonal kidney 293 cells (Do et al., 1997). Recently the inventors described LacdiNAc-based structures from transfected fibroblast cells (Saarinen et al., 1999). This study did not show if the glycosylation is related to cancer or to the transfection of the adenoviral EIA-promoter sequence to the cells as EIA-promoter may regulate the gene expression of glycosyltransferases and thereby modify the glycosylation. LacdiNAc type saccharides were also detected among other structures from tissue type plasminogen activator of Bowes melanoma cells, but these were considered to be "nervous system associated" structures (Jaques et al., 1996) The previous studies also describe the detection of similar oligosaccharide structures from cell lines derived from solid tumors (Do et al., 1997; Jaques et al., 1996; Saarinen et al., 1999). However, carbohydrate and other cell surface antigens usually change when contacts between cells are changed, for instance, when a solid tumor is divided to single cells. Besides, cells of cell lines are possibly genetically modified and only then cultured as single cells. Cell surface glycosylations are also very specific for the differentiation status of a cell line or tissue and they are specific for a cell or tissue type. Therefore prior art discussed herein do not describe the natural glycosylation status of a single cancer cell or solid tumor tissue. However, the potential correlations of the glycosylations with cell type or differentiation status allow the use of the cancer antigen(s) for the typing of cancer cells and tumors.

The following patents describe cancer antigens and their use for making antibodies for therapeutic and diagnostic uses and for cancer vaccines. The antigen structures are not related to saccharides of the present invention:

Cancer vaccines: U.S. Pat. No. 5,102,663 describes composition comprising 9-OAc NeuNAcα8NeuNAcα3Lac-Cer (GD3) for the stimulation or the enhancement of the production of antibodies against 9-OAc GD3.

U.S. Pat. No. 5,660,834 describes pharmaceutical composition containing mucin type glycoprotein consisting essentially of Tn (GalNAcα-Ser/Thr) or sialyl-Tn antigens (NeuNAcα6GalNAcα-Ser/Thr) and uses thereof with adjuvant to reduce cancer cell growth rate. Inventions related to the same mucin sequences are also described in other patents: U.S. Pat. No. 5,747,048 (adjuvant therapy for human) and U.S. Pat. No. 5,229,289.

U.S. Pat. No. 6,083,929 describes extended type 1 chain sphingolipids (Galβ3GlcNAc) as tumour-associated compositions and pharmaceutical composition with an adjuvant.

Therapeutic antibodies: U.S. Pat. No. 4,851,511 describes a monoclonal antibody that bind disialosyl Lewis a-structure NeuNAcα3Galβ3(Fucα4)[NeuNAcα6]GlcNAc, diagnostic test kits, hybridomas producings antibodies, marker molecules and an antitumor drug conjugated with antibodies.

U.S. Pat. No. 4,904,596 describes a monoclonal antibody that binds structure NeuNAcα3Galβ4(Fucα3) GlcNAcβ3Galβ4(Fucα3)GlcNAcβ3LacCer, hybridomas, diagnostics, and coupling of the antibody to an antitumor drug, an immunoregulatory agent or a differentiation inducing agent.

U.S. Pat. No. 5,874,060 describes humanized antibodies recognizing Lewis y-antigen Fucα2Galβ4(Fucα3)GlcNAc.

U.S. Pat. No. 6,025,481 describes nucleic acid molecules encoding humanized antibodies recognizing Lewis b-antigen. The Lewis b-structure Fucα2Galβ3(Fucα4)GlcNAc-expression is increased in cancer cells. U.S. Pat. No. 5,795,961 describes also anti-Lewis b antibodies.

Diagnostics: U.S. Pat. No. 4,725,557 describes protein linked antigens Fucα3Gal-, Fucα4Gal- and Fucα6Gal-, and antibodies recognizing these structures, method of determining the cancer associated carbohydrate linkages and diagnostic kits. The antibodies bind cancer cells of human digestive system.

U.S. Pat. No. 5,059,520 describes several monoclonal antibodies recognizing blood group A-antigen GalNAcα3 (Fucα2)Galβ-, which may be used for cancer diagnostics.

U.S. Pat. No. 5,171,667 describes antibodies against fucosylated type 2 lactosamines (-Galβ4(Fucα3)GlcNAcβ-) and use thereof for cancer diagnostics.

U.S. Pat. No. 5,173,292 describes monoclonal antibodies binding to Gal-globoside, Galβ3GalNAcβ3Galα4LacCer, which is a cancer specific structure.

U.S. Pat. Nos. 6,090,789 and 5,708,163 describe synthesis of Fucα2Galβ3GalNAcβ3Galα4LacCer (Globo H, MBr1, breast tumor associated antigen) conjugates and analogs thereof, and pharmaceutical compositions containing the same. U.S. Pat. No. 5,679,769 describes the synthesis of asparagines linked to glycopeptides. U.S. Pat. No. 5,543,505 describes synthetic compounds which bind *Helicobacter pylori* bacteria.

U.S. Pat. Nos. 5,902,725 and 6,203,999 describe the detection of prostate specific cancer by assaying at least triantennary oligosaccharides on prostate specific antigen. Antibody or lectin PHA-L is used for detection. The patents characterize chromatographically the presence of triantennary N-glycans on cancer form of PSA from a cell line.

The prior art describes fucosylated lacdiNAcs containing relatively large N-glycan structures (EP0565241) and a core 2-type O-glycan structures (EP0919563) in pharmaceutical compositions. The compositions are aimed for inhibition of selectin mediated cell adhesion and in EP0919563 also for inhibition of metastasis by inhibiting selectin mediated cell adhesion. However, the present invention is directed to the use of the oligosaccharide epitopes according to the present invention as targets of specific recognition molecules, including antibodies. The present invention is specifically directed to suitable antigenic conjugates and compositions for inducing antibodies for diagnostics and therapies. The present invention is directed to pharmaceutical compositions comprising optimal size of oligosaccharide sequences for recognition by specific antibodies. The optimal oligosaccharide epitopes may comprise only the terminal lacdinac structure or the terminal oligosaccharide sequence and one or two monosaccharide residues.

SUMMARY OF THE INVENTION

The present invention describes oligosaccharide sequences, which are specifically expressed by cancer cells. The present invention is related to a method of determining an oligosaccharide sequence, which comprises a cancer specific sequence of Formula

$$(Sac1)_x GalNAc\beta 4(Fuc\alpha 3)_y GlcNAc \qquad (I),$$

wherein x and y are each independently 0 or 1 and Sac1 is NeuNAcα3 or NeuNAcα6, in a biological sample, the presence of said sequence in said sample being an indication of the presence and/or type of cancer. The present invention provides antigenic substances comprising said oligosaccharide sequences in a polyvalent form and it further provides diagnostic agents, pharmaceutical compositions and cancer vaccines comprising said oligosaccharide sequences or substances binding to said oligosaccharide sequences. The present invention is also related to methods for the treatment of cancer.

DETAILED DESCRIPTION OF THE INVENTION

Figure 1A:
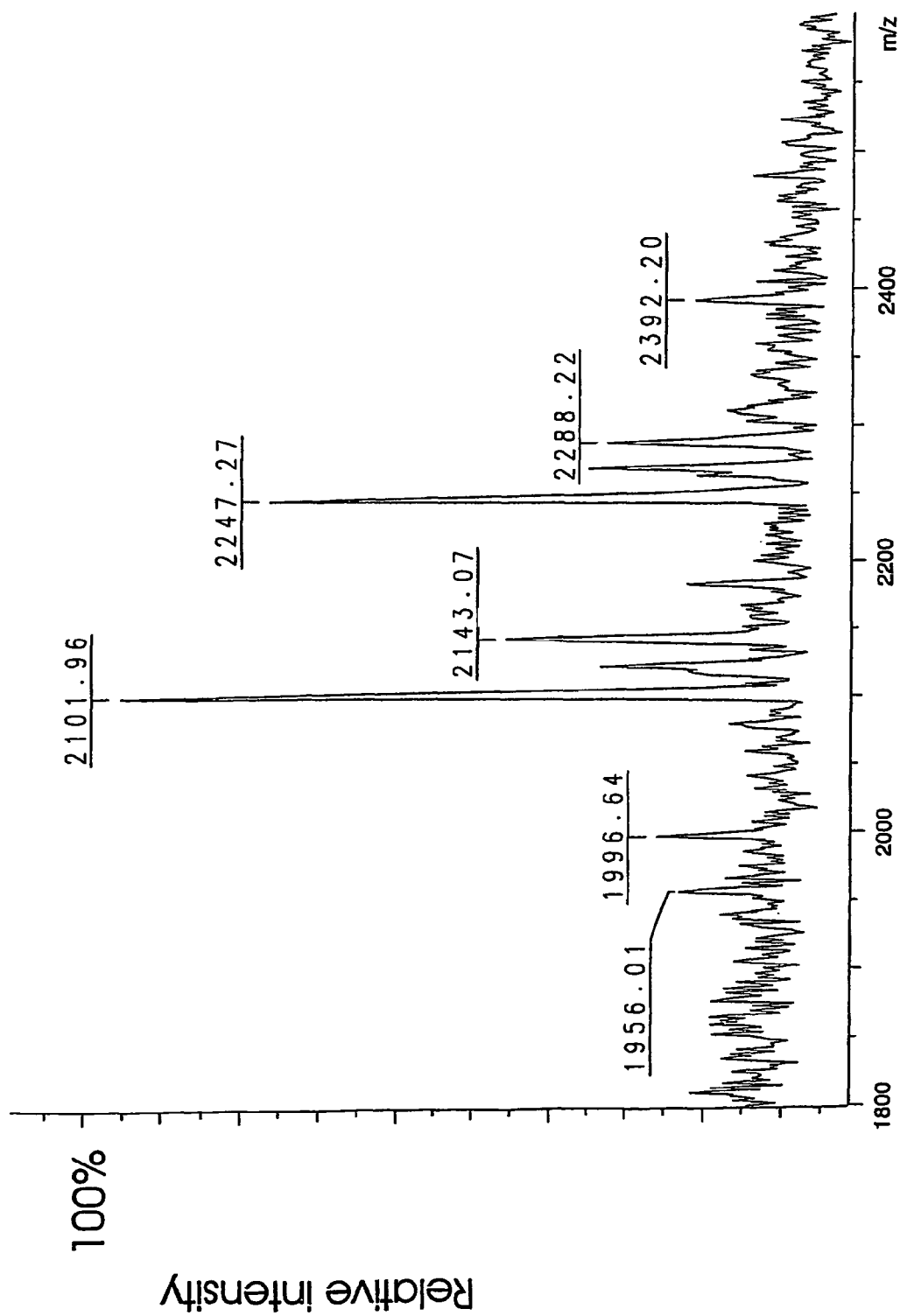
FIGS. 1A, 1B, 1C and 1D. MALDI TOF MS analysis of liberated MMP-9 N-glycans. (1A) intact N-glycans; (1B) the N-glycans after incubation with NDV neuramimidase, followed with consecutive treatments with (1C) *C. perfringens* neuraminidase and (1D) Almond meal fucosidase.

Several lacdiNAc (GalNAcβ4GlcNAc) type sequences are known from secretory proteins such as glycoprotein hormones. In human glycoprotein hormones the lacdiNAc is usually modified to 4sulfo-GalNAcβ4GlcNAc-sequences which are considered to be important for the hormone function, however, some heterogeneity exist in the secreted lacdiNAc-structures. The glycoprotein hormones are rare soluble proteins, relatively small in general and contain few glycosylation sites with quite limited selection of lacdiNAc structures. The lacdiNAc sequence has not been structurally characterized on human membrane-linked non-secreted proteins, though numerous structural studies of human glycosylations have carried out during last 30 years.

The role of lacdiNAc structures as an intracellular secretion marker has been demonstrated, the same report specifically states that lacdiNAc structures are not present on membrane proteins of MDCK cells (Ohkura, et al. 2001). The lacdiNAc structures characterized from secreted proteins have not been shown to be related to human cancer. The unusual expression of the lacdiNAc structures and especially rare fucosylated and sialylated variants thereof by cancers, but not on normal tissues, offer unusually good possibilities for cancer treatment and therapies based on the recognition of the structures. Diagnostic and therapeutic success have obtained by carbohydrates which are present on limited amount of normal tissues or in low density on normal tissues and/or in serum.

Methods Combining Diagnostics and Therapy for Effective Cancer Treatment

The data of present invention shows that lacdiNAc structures according to the present invention are useful for use of diagnostic and therapeutic methods which recognize the carbohydrate structures on cancer cells. As the glycosylation patterns varies between tissues, between different types of tumors and even between individual patients, the present invention is specifically directed to methods to screen unusual carbohydrate structures from tumors and direct individual therapy against the forms of glycosylation specifically expressed on the cancer of a specific patient. The present invention is specifically directed to the screening of lacdiNAc type glycosylations according to the present invention on tumor or cancer samples and using lacdiNAc targeting therapies according to the present invention for treatment of a patient who has the specific cancer associated glycosylation specifically on tumor or on malignant tissue or cells.

The inventors screened multiple normal tissues by effective mass spectrometric methods to verify that lacdiNAc is not cell surface marker on normal tissues. In the present invention it was found that (i) the lacdiNAc sequence occur in cancers both on unicellular cancer such as leukaemia and on solid tumors, (ii) the lacdiNAc sequence was not observable on multiple on normal tissues, (iii) the lacdiNAc sequence is present both on plasma membrane or membrane associated proteins and on secreted proteins of cancers, the integrated cell surface lacdiNAc sequences are targets for cancer diagnostics and immunotherapies and other therapies based to the recognition of the lacdiNAc sequences on cancers, and (iv) the lacdiNAc sequences on cancer cell surfaces can be recognized by specific antibodies for therapy and diagnostics. The structures are available on cell surfaces and not covered by other cell surface components.

Leukeamia cells were chosen as a model for unicellular cancer cells. The leukeamia cells represent the unicellular cancer cells in the blood cancers. The soluble target protein was chosen so that structural comparison data from non-malignant cells exists. To demonstrate abnormal expression of LacdiNAc sequence on cancer cells metalloproteinase-9 (MMP-9) was isolated from leukaemia cells (U-937), and N-glycosidic glycans were liberated with N-glycosidase F. The glycan fraction was analyzed with MALDI-TOF MS in trihyxroacetophenone matrix (FIG. 1A), which has been shown to cause negligible fragmentation of sialic acid residues. The assignment of the monosaccharide compositions as well as the proposed structures according to the subsequent glycosidase treatments are shown in Table 1. The relative abundances of the components are indicated as well, as oligosaccharide analysis in MALDI-TOF has been shown to be relatively quantitative. The most abundant glycan species was assigned to $[M+Na]^+$ of $(Hex)_5(HexNAc)_4(Fuc)_3$. Knowing the typical N-glycan structures, we tentatively assigned this structure as a trifucosylated diantennary complex-type glycan. Other major species were identified as sialylated, difucosylated diantennary complex-type glycan, and trifucosylated diantennary complex-type glycan carrying GalNAc instead of Gal as a terminal monosaccharide (so called LacdiNAc structure) in one antennae. These assignments were found to be correct, as shown by sequential glycosidase treatments. For comparison the matrix metalloproteinase MMP-9 structures in non-malignant white blood cells (leukocytes) have been determined, the protein did not contain lacdiNAc sequences (Rudd P et al, 1999).

The present invention shows that U-937-cell derived MMP-9 carries LacdiNAc structures in large fraction (approximately 30%) of its N-glycans. The presence of LacdiNAc structures was verified by two independent methods, namely MALDI-TOF analysis of liberated N-glycans as well as LC-ESI MS of intact glycopeptides. The assignments of the structures were further confirmed by sequential glycosidase treatments. The methods used in this study have been verified by several approaches using both known natural structures as well as synthetic oligosaccharides.

Mass Spectrometric Screening of lacdinac-Structures from Normal Tissues

Membrane glycoprotein samples of several non-malignant tissues, including human stomach, lungs, and colon were analyzed mass spectrometric methods as described above. No N-linked or O-linked type lacdiNAc-sequences were observed. The prior art does not describe lacdiNac on human normal or cancer membrane proteins either.

Analysis of lacdiNAc Structures on Solid Tumors

The present invention demonstrates also for the first time that lacdiNAc-sequences are present on human solid tumors. An example of the present inventions shows characterization of lacdiNAc structure from sample of cancer of human larynx.

Characterization of lacdiNAc Sequences from Plasmamembrane Samples

The present invention is also directed to the plasmamembrane forms of lacdiNAc expressing proteins on cancers. The matrix metalloproteinase MMP-9 is also known to occur as membrane associated form (Koivunen et al., 1999), which according to present invention also form ideal target for cancer diagnostics and immune therapy. As another example, glycosylations of two different samples of melanoma related membranes were analyzed. Large amounts of various lacdiNAc-type oligosaccharide sequences were found on the membrane bound glycoproteins including unique N-glycan structures. The glycosylated membrane proteins are known to be presented on the surface of the cells and tissues.

Specific Defect in Cancer Demonstrated by the Present Invention

The present invention shows a novel defect in cancer cells. The rare structure associated with secretory proteins is expressed on proteins which normally do not express the lacdiNAc structures. Furthermore the failure in glycosylation induces more unusual sialylated, fucosylated, and variants without usual sulphation on position 4 of GalNAc. A general understanding about the cancers are that the intracellular organization of cancer cells is disturbed. Such errors in Golgi apparatus which produces very specific glycosylations on different cell types obviously leads to the problems described. Obviously presence of the cancer indicating abnormal glycosylations on soluble proteins is useful for cancer diagnostics, the presence of the cancer glycosylation associated with membranes makes these directly useful for therapeutics.

As described above the presence of cancer antigens was studied from secreted MMP-9 protein of leukaemia cell line U-937 from solid tumors, and from membrane preparations. The single cells of a leukemia cell line are also considered to be a reasonably relevant model of single cell cancer leukaemia. Demonstration of the lacdiNAc-structures from solid tumors and being membrane associated shows the usefulness of the cancer glycosylation for therapies against solid tumors expressing the glycosylation.

The present invention shows that LacdiNAc structures according to Formula $$(Sac1)_x GalNAc\beta 4 (Fuc\alpha 3)_y GlcNAc \qquad (I)$$

wherein x and y are each independently 0 or 1 and Sac1 is NeuNAcα3 or NeuNAcα6, are cancer specific antigens. The invention is directed to the detection of the cancer antigens directly from cancer cells and tumor tissues as a cell-associated form of MMP-9 is known (Koivunen et al., 1999). However, the cancer antigens may, in addition to the detection from cancer cells and tumor tissues, be detected, as described herein, on a secreted glycoprotein derived from cancer cells or tissues. The cancer specific proteins can be proteinases, hormones or secreted mucin type glycoproteins.

The present invention shows that a cancer antigen can be detected from a glycoprotein, which is known to be upregulated upon malignant transformation. The presence of the cancer antigen on a putative cancer associated glycoprotein may provide a more reliable diagnostic tool of cancer in early phase. Examples of such preferred cancer associated proteins include, but are not limited to, members of matrix metalloproteinase protein family (e.g. MMP-9), prostate specific antigen, kallikrein 2, human chorionic gonadotrophin and carcinoembryonic antigen.

Cancer specific oligosaccharides of the LacdiNAc type contains GalNAcβ4GlcNAc-oligosaccharide sequence. The sequence is a part of an oligosaccharide glycoconjugate of cancer cells. The oligosaccharide sequence can be substituted to sequence GalNAcβ4(Fucα3)GlcNAc-, NeuNAcα3GalNAcβ4GlcNAc-, NeuNAcα6GalNAcβ4GlcNAc-, NeuNAcα3GalNAcβ4 (Fucα3)GlcNAc-, or NeuNAcα6GalNAcβ4(Fucα3) GlcNAc-, which were also indicated to be present on the cancer cells. If a single cancer oligosaccharide epitope contains both sialic acid and fucose the structure can be NeuNAcα3GalNAcβ4(Fucα3)GlcNAc-. The LacdiNAc sequence can also be sulphated, for instance, to position 4 of GalNAc, if the cancer cells contain a sulphotransferase needed for the modification. The LacdiNAc-type sequence(s) can be a part of a glycoprotein sequence of cancer cells or tissue, for instance, LacdiNAc type sequence is β2-, β4- or β6-linked to a mannose residue in a N-linked glycan of a glycoprotein, or the LacdiNAc-sequence is β2-linked to a mannose residue in a N-linked glycan of a glycoprotein.

The fucosylated LacdiNAc saccharides are analogous to Lewis type cancer associated oligosaccharides. Potential weak cross reactivity with fucosylated LacdiNAcs is a probable explanation for the production of human antibodies weakly recognizing Lewis type cancer associated oligosaccharides though these are present in large amounts also in normal tissues.

The present invention also describes methods to detect malignancy of a cell or a tissue by detecting cancer specific glycosylations. The detection can be performed by molecules specifically binding to the cancer specific oligosaccharide sequences of the invention. Preferably the molecules specifically binding to the cancer specific oligosaccharide sequences are aptamers, lectins, genetically engineered lectins, antibodies, monoclonal antibodies, antibody fragments, enzymes recognizing LacdiNAc-structure such as glycosidases and glycosyltransferase and genetically engineered variants thereof. Labelled bacteria, viruses or cells or other polymeric surfaces containing molecules recognizing the structures can be used for the detection. Oligosaccharide sequences can also be released from cancer cells by endoglycosidase enzymes. Alternatively oligosaccharides can be released as glycopeptides by protease enzymes. Chemical methods to release oligosaccharides or derivatives thereof include, e.g., otsonolysis of glycolipids and beta-elimination or hydrazinolysis methods to release oligosaccharides from glycoproteins. Alternatively the glycolipid fraction can be isolated. A substance specifically binding to the cancer specific oligosaccharide sequences can also be used for the analysis of the same sequences on cell surfaces. Said sequences can be detected, e.g., as glycoconjugates or as released and/or isolated oligosaccharide fractions. The possible methods for the analysis of said sequences in various forms also include NMR-spectroscopy, mass spectrometry and glycosidase degradation methods. Preferably at least two analysis methods are used, especially when methods of limited specificity are used.

Mass spectrometry is a preferred method to determine the cancer specific oligosaccharide sequence or sequences according to the invention in a sample. Mass spectrometric scanning methods for the detection of HexNAc-HexNAc-fragments from a fraction containing oligosaccharide sequences according to Formula I are especially preferred.

The present invention is also directed to the use of cancer specific oligosaccharide sequences or analogs or derivatives thereof to produce polyclonal or monoclonal antibodies recognizing the structures using following process: 1) producing synthetically or biosynthetically a polyvalent conjugate of an oligosaccharide sequence of the invention or an analogue or derivative thereof, the polyvalent conjugate being, for instance, according to the following structure: position C1 of reducing end terminal of the oligosaccharide sequence (OS) comprising the cancer specific terminal sequence of the invention is linked (-L-) to an oligovalent or a polyvalent carrier (Z), via a spacer group (Y) and optionally via a monosaccharide or oligosaccharide residue (X), forming a structure according to Formula $$[OS\!-\!(X)_n\!-\!L\!-\!Y]_m\!-\!Z \qquad (II),$$

where integer m has values m>1, and n is independently 0 or 1; L is oxygen, nitrogen, sulfur or carbon atom, X is preferably lactosyl-, galactosyl-, poly-N-acetyl-lactosaminyl-, or part of an O-glycan or an N-glycan oligosaccharide sequence, Y is a spacer group or a terminal conjugate such as a ceramide lipid moiety or a linkage to Z; preferably one of the following properties are present: the oligosaccharide sequence (OS) is sialylated, X comprises at least one mannose or N-acetylgalactosamine residue or Z comprises a carbohydrate material, such as a polysaccharide; 2) immunizing an animal or human with the polyvalent conjugate together with an immune response activating substance. Preferably the oligosaccharide sequence is polyvalently conjugated to the immune response activating substance and the conjugate is used for immunization alone or together with an additional immune response activating substance. In a preferred embodiment the oligosaccharide conjugate is injected or administered mucosally to an antibody producing organism with an adjuvant molecule or adjuvant molecules. For antibody production the oligosaccharide or analogs or derivatives thereof can be polyvalently conjugated to a protein such as BSA, keyhole limpet hemocyanin, a lipopeptide, a peptide, a bacterial toxin, a part of peptidoglycan or immunoactive polysaccharide or to another antibody production activating molecule. The polyvalent conjugates can be injected to an animal with adjuvant molecules to induce antibodies by routine antibody production methods known in the art. Preferably an antigenic substance of the invention comprises a terminal oligosaccharide sequence as defined in Formula I in a chemically or biochemically synthezised polyvalent form described above for immunization in human. More preferably the antigenic substance comprises terminal NeuNAcα3 or NeuNAcα6 (i.e. x=1 in Formula I) or the saccharide sequence is linked to mannose or N-acetylgalactosamine (e.g. X is Man or GalNAc in Formula II).

The present invention is also directed to monovalent and/oligovalent antigenic conjugates of oligosaccharide sequences according to the present invention. Monovalent antigenic conjugate may comprise an antigenic lipid structure, for example a ceramide, a synthetic lipid or a bacterial type of lipid which can induce antibody production as described by the invention and by methods known in the art.

The present invention is specifically directed to the use of optimal size antigenic epitopes and pharmaceutical compositions comprising these. Antibodies can usually recognize effectively only epitopes of a few monosaccharide residues. Reduced size of the epitope is also preferred because of more cost effective synthesis of the structures.

Preferred optimal antigenic epitopes includes structures according to the Formula II

wherein Y is a non-carbohydrate spacer or a non-glycosidically linked terminal conjugate, n is 0 or 1 and X is lactosyl-, galactosyl-, N-acetyllactosaminyl, mannosyl-, $Man_2$, $Man_3$-, $Man_3GlcNAc$, $Man_4GlcNAc$, N-acetylglucosaminyl-, or N-acetylgalactosaminyl. More preferably X is lactosyl-, galactosyl-, mannosyl-, or N-acetylgalactosaminyl. In a preferred embodiment the OS is β2-, or β4, or β6 linked to the mannosylresidue, most preferably β2-. In a preferred embodiment the OS is β3- or β6-linked to galactosylresidue or N-acetylgalactosaminylresidue or Gal-residue of lactose or N-acetylalactosamine, more preferably β3- or β6-linked to Gal or Gal of lactose or to GalNAc, and most preferrably β3-linked to Gal or Gal of lactose or β6-linked to GalNAc. In a preferred embodiment the optimal antigenic epitopes as described above does not comprise fucose in the oligosaccharide sequence.

$Man_2$, $Man_3$-, $Man_3GlcNAc$, $Man_4GlcNAc$ indicates preferably parts of N-glycan core structures comprising oligosaccharide sequences Manα3Man, Manα6Man, Manα3 (Manα6)Man, Manα3(Manα6)Man, Manα3(Manα6) Manα4GlcNAc and hydrid type of structure wherein additional mannose is linked to either non-reducing terminal Man, preferably Manα6 branch, and the oligosaccharide sequence according to the present invention to the other branch of the molecule.

In a preferred embodiment optimal antigenic epitope comprising structures OSβ2Man, OSβ2Manα3Man, or OSβ2Manα6Man are used. These are partial epitopes of the N-glycan lacdiNAc primarily observed by the present invention. In a separate embodiment it is also realized that because of the glycosylation defects in cancer cells, O-glycan type lacdiNAc and partial lactosamine type lacdiNAcs comprising similar optimal antigenic epitopes OSβ3Gal, OSβ3GalNAc and especially OSβ6Gal, OSβ6GalNAc are useful for immunization and other uses according to the present invention against tumors comprising these structures. Such tumors are characterized by lacdiNAc type secretory functions combined with lactosamine and or mucin production.

The cancer specific oligosaccharides or derivatives or analogs thereof can be immobilized for the purification of antibodies from serum, preferably from human serum. The cancer specific oligosaccharides, preferably as polyvalent conjugates, can also be used for the detection and/or quantitation of antibodies binding to these cancer specific oligosaccharides, for example, in enzyme-linked immunosorbent assay (ELISA) or affinity chromatography type assay formats for the diagnostics of cancer.

Antibody production or vaccination can be also achieved by analogs or derivatives of the cancer specific oligosaccharide sequences. Simple analogs of the N-acetyl-group containing oligosaccharide sequences include compounds with modified N-acetyl groups, for example, N-acyl such as N-propanoyl. The present invention is also directed for production of specific analogs for the cancer specific oligosaccharide sequences as described by the invention.

Furthermore, it is possible to use human antibodies or humanized antibodies against the cancer specific oligosaccharide sequences to reduce the growth of or to destroy a tumor or cancer. Human antibodies can also be tolerated analogs of natural human antibodies against the cancer specific oligosaccharide sequences; the analogs can be produced by recombinant gene technologies and/or by biotechnology and they may be fragments or optimized derivatives of human antibodies. Purified natural anti-tumor antibodies can be administered to a human without any expected side effect as such antibodies are transferred during regular blood transfusions. This is true under conditions that the cancer specific structures are not present on normal tissues or cells and do not vary between individuals as blood group antigens do, however, such blood-group-like variations are not known for the cancer specific oligosaccharide sequences of the invention. In another embodiment of the invention species specific animal antibodies are used against a tumor or cancer of the specific animal. The production of specific humanized antibodies by gene engineering and biotechnology is also possible: the production of humanized antibodies has been described in U.S. Pat. Nos. 5,874,060 and 6,025,481, for example. The humanized antibodies are designed to mimic the sequences of human antibodies and therefore they are not rejected by immune system as animal antibodies are, if administered to a human patient. It is realized that the method to reduce the growth of or to destroy cancer applies both to solid tumors and to cancer cells in general. It is also realized that the purified natural human antibodies recognizing any human cancer specific antigen, preferably an oligosaccharide antigen, can be used to reduce the growth of or to destroy a tumor or cancer. In another embodiment species specific animal antibodies are used against a tumor or cancer of the specific animal.

According to the invention human antibodies or humanized antibodies against the cancer specific oligosaccharides, or other tolerated substances binding the cancer specific oligosaccharides, are useful to target toxic agents to tumor or to cancer cells. The toxic agent could be, for example, a cell killing chemotherapeutics medicine, such as doxorubicin (Arap et al., 1998), a toxin protein, or a radiochemistry reagent useful for tumor destruction. Such therapies have been demonstrated and patented in the art. The toxic agent may also cause apoptosis or regulate differentiation or potentiate defence reactions against the cancer cells or tumor. In another embodiment of the invention species specific animal antibodies are used against a tumor or cancer of the specific animal. The cancer binding antibodies according to the present invention can also be used for targeting prodrugs active against cancer or enzymes or other substances converting prodrugs to active toxic agents which can destroy or inhibit cancer, for example in so called ADEPT-approaches.

The therapeutic antibodies described above can be used in pharmaceutical compositions for the treatment or prevention of cancer. The method of treatment of the invention can also be used when patient is under immunosuppressive medication or he/she is suffering from immunodeficiency.

Immunosuppressive medications are used, for instance, with organ transplantations to prevent rejection during kidney, heart, liver or lung transplantations. Malignancies arising during such therapies are in general benign, but they cause often the loss of the precious organ transplant. Capability of producing antibodies against the tumor or cancer specific antigens may vary according to individual differences in immune system. Persons who have survived from cancer may have especially high amounts of natural anti-cancer antibodies.

Other Methods for Therapeutic Targeting of Cancers

It is realized that numerous other agents beside antibodies, antibody fragments, humanized antibodies and the like can be used for therapheutics targeting cancers similarly with the diagnostic substances. It is specifically preferred to use non-immunogenic and tolerable substances to target cancer. The targeting substances binding to the cancer comprise also specific toxic or cytolytic or cell regulating agents which lead to destruction or inhibition of cancer. Preferably the non-antibody molecules used for cancer targeting therapies comprise molecules specifically binding to the cancer specific oligosaccharide sequences according to the present invention are aptamers, lectins, genetically engineered lectins, enzymes recognizing LacdiNAc-structure such as glycosidases and glycosyltransferase and genetically engineered variants thereof. Labelled bacteria, viruses or cells or other polymeric surfaces containing molecules recognizing the structures can be used for the cancer targeting therapies. The cancer binding non-antibody substances according to the present invention can also be used for targeting prodrugs active against cancer to cancers or enzymes or other substances converting prodrugs to active toxic agents which can destroy or inhibit cancer.

The present invention is specifically directed to the use of substances and antibodies binding to cancer specific oligosaccharide sequences according to the present invention for therapies in gastrointestinal tract of the patient, preferably in human patient. The therapeutic antibodies for use in human gastrointestinal tract may be antibodies produced by animals for example antibodies in milks of domestic animals, for example in milk of domestic ruminants such as cows, sheep, goat or buffalo or antibodies produced in hen eggs. The animals can be immunized by cancer specific carbohydrate conjugates as known in the art. The present invention is also directed to other acceptable, preferably food acceptable proteins which can be used in inhibition or destruction of cancers in human gastrointestinal tract, such substances include plant lectins which are specific for the cancer specific oligosaccharide sequences. The present invention is directed to functional foods and food additives containing antibodies recognizing the cancer specific oligosaccharide sequences according to the present invention in gastrointestinal tract, the present invention is also directed to the use of other food acceptable substances especially lectins binding to the cancer specific oligosaccharide sequences of gastrointestinal tract in functional foods or as food additives.

Furthermore according to the invention the cancer specific oligosaccharide sequences or analogs or derivatives thereof can be used as cancer vaccines in human to stimulate immune response to inhibit or eliminate cancer cells. The treatment may not necessarily cure cancer but it can reduce tumor burden or stabilize a cancer condition and lower the metastatic potential of cancers. For the use as vaccines the oligosaccharides or analogs or derivatives thereof can be conjugated, for example, to proteins such as BSA or keyhole limpet hemocyanin, lipids or lipopeptides, bacterial toxins such as cholera toxin or heat labile toxin, peptidoglycans, immunoreactive polysaccharides, or to other molecules, cells or cell preparations activating immune reactions against a vaccine molecule. A cancer vaccine may also comprise a pharmaceutically acceptable carrier and optionally an adjuvant. Suitable carriers or adjuvants are, e.g., lipids known to stimulate the immune response. The saccharides or derivatives or analogs thereof, preferably conjugates of the saccharides, can be injected or administered mucosally, such as orally or nasally, to a cancer patient with tolerated adjuvant molecule or adjuvant molecules. The cancer vaccine can be used as a medicine in a method of treatment against cancer. Preferably the method is used for the treatment of a human patient. Preferably the method of treatment is used for the treatment of cancer of a patient, who is under immunosuppressive medication or the patient is suffering from immunodeficiency.

Furthermore it is possible to produce a pharmaceutical composition comprising the cancer specific oligosaccharide sequences or analogs or derivatives thereof for the treatment of cancer. Preferably the pharmaceutical composition is used for the treatment of a human patient. Preferably the pharmaceutical composition is used for the treatment of cancer, when patient is under immunosuppressive medication or he/she is suffering from immunodeficiency. The methods of treatment or the pharmaceutical compositions described above are especially preferred for the treatment of cancer diagnosed to express the cancer specific oligosaccharide sequences of the invention. The methods of treatment or the pharmaceutical compositions can be used together with other methods of treatment or pharmaceutical compositions for the treatment of cancer. Preferably the other methods or pharmaceutical compositions comprise cytostatics, anti-angiogenic pharmaceuticals, anti-cancer proteins, such as interferons or interleukins, or a use of radioactivity.

Use of antibodies for the diagnostics of cancer and for the targetting of drugs to cancer has been described with other antigens and oligosaccharide structures (U.S. Pat. No. 4,851,511; U.S. Pat. No. 4,904,596; U.S. Pat. No. 5,874,060; U.S. Pat. No. 6,025,481; U.S. Pat. No. 5,795,961; U.S. Pat. No. 4,725,557; U.S. Pat. No. 5,059,520; U.S. Pat. No. 5,171,667; U.S. Pat. No. 5,173,292; U.S. Pat. No. 6,090,789; U.S. Pat. No. 5,708,163; U.S. Pat. No. 5,902,725 and U.S. Pat. No. 6,203,999). Use of cancer specific oligosaccharides as cancer vaccines has also been demonstrated with other oligosaccharide sequences (U.S. Pat. No. 5,102,663; U.S. Pat. No. 5,660,834; U.S. Pat. No. 5,747,048; U.S. Pat. No. 5,229,289 and U.S. Pat. No. 6,083,929).

The substance according to the invention can be attached to a carrier. Methods for the linking of oligosaccharide sequences to a monovalent or multivalent carrier are known in the art. Preferably the conjugation is performed by lining the cancer specific oligosaccharide sequences or analogs or derivatives thereof from the reducing end to a carrier molecule. When using a carrier molecule, a number of molecules of a substance according to the invention can be attached to one carrier increasing the stimulation of immune response and the efficiency of the antibody binding. To achieve an optimal antibody production, conjugates larger than 10 kDa carrying typically more than 10 oligosaccharide sequences are preferably used.

The oligosaccharide sequences according to the invention can be synthesized, for example, enzymatically by glycosyltransferases, or by transglycosylation catalyzed by a glycosidase enzyme or a transglycosidase enzyme, for review see Ernst et al., 2000. Specificities of the enzymes and their use of co-factors such as nucleotide sugar donors, can be engineered. Specific modified enzymes can be used to obtain more effective synthesis, for example, glycosynthase is modified to achieve transglycosylation but not glycosidase reactions. Organic synthesis of the saccharides and conjugates of the invention or compounds similar to these are known (Ernst et al., 2000). Carbohydrate materials can be isolated from natural sources and be modified chemically or enzymatically into compounds according to the invention. Natural oligosaccharides can be isolated from milks of various ruminants and other animals. Transgenic organisms, such as cows or microbes, expressing glycosylating enzymes can be used for the production of saccharides.

It is possible to incorporate an oligosaccharide sequence according to the invention, optionally with a carrier, in a pharmaceutical composition, which is suitable for the treatment of cancer in a patient. Examples of conditions treatable according to the invention are cancers in which the tumor expresses one or more of the cancer specific oligosaccharides described in the invention. The treatable cancer cases can be discovered by detecting the presence of the cancer specific oligosaccharide sequences in a biological sample taken from a patient. Said sample can be, e.g., a biopsy or a blood sample.

It is possible to inhibit the formation of cancer antigens described in the invention by specific inhibitors of LacdiNAc biosynthesis. Such inhibitors maybe analogs of donor nucleotide UDP-GalNAc. Methods to produce inhibitory analogs for glycosyltransferases have been described in the art. Preferably the inhibitor has specificity towards LacdiNAc synthezising GalNAc-transferase.

Alternatively an essentially non-antigenic chemically and/or enzymatically synthesised oligo- or polyvalent conjugate of the cancer specific oligosaccharide sequences of the invention can be used to prevent the adhesion and/or growth of cancer cells. As the antigenicity of the conjugates would cause the removal of inhibitory oligomers or polymers from blood circulation by antibodies. Examples of antigenic substances of the invention have been described above. A non-antigenic polysaccharide conjugate can be constructed according to Formula II with the proviso that X, Y or Z are not immunogenic. Preferably the molecular weight of the conjugate is under 50 kilodaltons (kDa) and more preferably under 10 kDa. The oligosaccharide sequences of the invention can also be conjugated to a non-protein carrier. Preferably the cancer specific oligosaccharide sequence is conjugated to a non-immunogenic polysaccharide and most preferably the molecular weight of the conjugate is under 10 kDa.

As selectin carbohydrate interactions mediate cancer metastasis, the LacdiNAc-type glycosylations may target metastasing cancer cells to selectin containing sites on blood vessel endothelium as such structures are known to be potent selectin ligands (Grinnel et al., 1994; Jain et al., 1998). LacdiNAc saccharides have immunomodulatory activities which may protect them from immune response as discussed in Dell et al. (1995). The terminal GalNAc residues may also target cancer cells towards asialoglycoprotein receptors of liver (Yang et al., 2000). By preventing LacdiNAc-biosynthesis in cancer cells the metastatic potential and possibly the malignancy of the cancer is reduced. The present invention is especially directed to the prevention of lacdiNAc biosynthesis for prevention of metastatic potential of cancer cells. The optimal antigenic epitopes are not designed as metastasis inhibitors. The vaccine type approach uses really low amounts of lacdiNAc structures so that selectin mediated cell adhesion, which is necessary also for normal immune system and leukocyte function, is not prevented.

The pharmaceutical composition according to the invention may also comprise other substances, such as an inert vehicle, or pharmaceutically acceptable carriers, preservatives etc., which are well known to persons skilled in the art.

The substance or pharmaceutical composition according to the invention may be administered in any suitable way. Methods for the administration of therapeutic antibodies or vaccines are well-known in the art.

The term "treatment" used herein relates to both treatment in order to cure or alleviate a disease or a condition, and to treatment in order to prevent the development of a disease or a condition. The treatment may be either performed in a acute or in a chronic way.

The term "patient", as used herein, relates to any mammal in need of treatment according to the invention.

When a cancer specific oligosaccharide or compound specifically recognizing cancer specific oligosaccharides of the invention is used for diagnosis or typing, it may be included, e.g., in a probe or a test stick, optionally in a test kit. When this probe or test stick is brought into contact with a sample containing antibodies from a cancer patient or cancer cells or tissue of a patient, components of a cancer positive sample will bind the probe or test stick and can be thus removed from the sample and further analyzed.

In the present invention the term "cancer" means "tumor" or "cancer cells". The term "tumor" means solid multicellular tumor tissues. Furthermore the term "tumor" means herein premalignant tissue, which is developing to a solid tumor and has cancer specific characteristics. The term "tumor" is not referring herein to a single cell cancer such as a leukaemia or to cultured cancer cells or a cluster of such cells. The expression "cancer cells" means herein cells in tumor or single cancer cells such as leukaemia cells or any other type of malignant cells, which are developing to a cancer or tumor form and have cancer or cancer specific characteristics.

Enzymatic Synthesis of lacdiNAc Structures and Fucosylated lacdiNAc Structures and Analogs Thereof.

Terminal lacdiNac epitope can be synthesized by using large amounts of β4-galactosyltransferase (e.g. a commercially available bovine milk galactosyltransferase) and molar excess of UDP-GalNAc in comparison to the acceptor. For example incubations of UDP-GalNAc with GlcNAcβ3Galβ4Glc with relatively large amounts of β4-galactosyltransferase as described in (Nyame, et al 2000) gives GalNAcβ4GlcNAcβ3Galβ4Glc.

The reactions can also be performed by novel recombinant form of galactosyltransferase which can transfer GalNAc effectively from UDP-GalNAc (Ramakrishnan et al., 2001).

The GalNAcβ4GlcNAc epitope or its sialylated derivative NeuNAcα3GalNAcβ4GlcNAc can be fucosylated by several types of α3-fucosyltransferases, for example by fucosyltransferases from human milk essentially as described in Bergwerff et al. 1993 or by fucosyltransferase VI.

Production of Novel GalN Derivatives, Especially lacdiNac Structures and Analogs Thereof Present invention is also directed to novel pathways of enzymatic synthesis. These can be used in vitro for production of lacdiNac-structures, related structures and analogs. Prior art has described glycosidase reactions on hexosamines and use of hexosamine donors for glycosidase reactions. The present invention is directed to the use of terminal hexosamines especially galactosamine and GalNβ4Glc(NAc)-terminal structures as acceptors for various glycosyltransferases which normally use acceptor structures comprising for example terminal Gal or GalNAc residue.

These reactions have not previously been described and the positive charge of amine group close to negatively charged nucleotide sugar donor could have prevented the reactions. The charged aminogroup could also prevent recognition by enzymes requiring hydroxyl group in 2-position of the acceptor or cause undesired irreversible binding to the active site of the enzyme. The present invention shows for the first time that the novel glycosyltransferase reactions are possible and that the reactions are possible even by mammalian glycosyltransferases. In comparison to glycosidase catalysed reactions the glycosyltransferase reactions are specific forming in general only one type of products from a pair of donor and acceptor substrates, while the glycosidase catalysed transglycosylation reaction yield in general several products.

Previously lacdiNAc derivatives have been synthesized by forcing the enzymes using Gal acceptors to use GalNAc. Yields in these methods are in general very poor. Some of the reactions with certain transferases may not be more effective than reactions with terminal GalNAc, but the presence of amine allows specific synthesis of amine derivatives or analogs of natural Gal/GalNAc sequences.

The novel reactions also reveal potential biosynthetic pathways to novel malignant or disease associated antigenic structures, which have not been characterized from normal tissues. Especially novel blood group related antigens are produced by natural glycosylation enzymes.

Preferred reactions include glycosyltransferase reactions to 3, 4, or 6 position of the terminal hexosamine, preferably galactosamine and more preferably to 3 or 6 position of the galactosamine and most preferably to 3-position of galactosamine. Preferred reactions include: α3-sialyltransferase reactions, α6-sialyltransferase reactions, α3-galactosyltransferase reactions, α3-N-acetylgalactosaminyltransferase reactions, α3-galactosaminyltransfer reactions, β3-N-acetylglucosaminyl reactions, β6-N-acetylglucosaminyl reactions, β3-N-acetylgalactosamiyl reactions, β3-glucuronyltransferase reactions. Most preferred reactions include α3-sialyltransferase reactions, α3-glalactosaminyltransfer reactions and α3-galactosyltransferase reactions.

Preferred synthesis reactions are according to the formula

SAC-donor+GalNβ3/4→SACyxGalNβ3/4    (I)

wherein y is α- or β-linkage and independently x is linkage position 3, 4, or 6, SAC is sialic acid, or $Hex(A)_{s1}[N(Ac)_{s2}]_{s3}$ wherein Hex is Gal or Glc and s1, s2, s3 are independently 0 or 1, with the proviso that when s1 is 1, then s3 is 0. When s1 is 1, the SAC-structure comprises hexuronic acid structure, preferrably GlcA. When s3 is 1 and s2 is 1, the SAC-structure is GlcNAc or GalNAc, and when s2 is 0 the structure is GalN or GlcN. GalNβ3/4 indicates nonreducing terminal GalN which is β3- or β4-linked to a hexose or hexosamine or hexosamine derivative, preferrably Gal, GalN, GalNAc, Glc, GlcN, or GlcNAc. In a preferred embodiment GalNβ4 is part of non reducing terminal structure GalNβ4GlcNAc or GalNβ4Glc, for example GalNβ4GlcNAcβ3Galβ4Glc.

The present invention is further directed to novel carbohydrate substances according to the formula $Gal[N(Am)_{s2}]_{s3}α3GalN(Am)_{s2}β3/4$    (IV)

wherein Am is a derivatization residue of amine amine group, with the provision that Am is not acetyl (Ac) or an imidogroup, preferably Am is carboxylic acid forming amide with the GalN residue such as formamide, propanoic acid amide, and other alkyl amides, and cyclic amides including amides of cyclohexane radical comprising carboxylic acid and amides with aromatic hydrocarbons, for example amides of benzoic acids. Acetyl group is not preferred for the analog substances as it is present in natural oligosaccharide sequences, bulky imidogroups such as phtalimido-group is not preferred because of the large size of the group which would change too much the conformation of the analog s2, s3 are independently 0 or 1.

More preferred substances include terminal oligosaccharide sequences $Gal[N(Am)_{s2}]_{s3}α3GalN(Am)_{s2}β4GlcNAC$ and $Gal[N(Am)_{s3}]α3GalN(Am)_{s2}β4Glc$ And most preferred terminal oligosaccharide sequences includes $Galα3GalN(Am)_{s2}β4GlcNAc$, $Galα3GalN(Am)_{s2}β4Glc$, and Galα3GalNβ4GlcNAc and Galα3GalNβ4Glc.

The novel substances are especially useful for use as antigens and immunization. The rare and mostly non-natural or pathogenesis related structures are useful immunogens which can be used for inducing production of antibodies which also recognize related structures. Amine containing substances are also useful starting materials for production of further analogs, for testing as glycosidase substrates and/or inhibitors and testing as analogs of natural oligosaccharide sequences for binding of animal or plant lectins.

The present invention is also directed to combined reactions in which UDP-GalN is first transferred to acceptor, for example to GlcNAc or Glucose or non-reducing end terminal GlcNAc or glucose and in the same reaction vessel the GalN is modified to 3, 4, or 6-position, preferably to 3, or 6 position and most preferably to 3 position. In another combined reaction UDP-GalN is formed simultaneously in the same reaction with two glycosyltransferases. Methods to produce UDP-GalN in situ for the reaction have been previously described.

The present invention preferably uses a simplified process in which UDP-GalN is generated from GalN1-phosphate and UDP-Glc. Preferred embodiment about synthesis of lacdiNAc-type structures include N-acetylation of the hexosamine preferably to N-acetylhexosamine such as GalN to GalNAc.

In a preferred embodiment, analogs of an N-acetylhexosamine or hexose comprising oligosaccharides are produced, preferably lacdiNAc analog products are desired. The present invention is also directed to production of amine derivatives of the hexosamine, preferred amine analogs or derivatives of hexosamine include amides such as formamide, propanoic acid amide, and other alkyl amides, and cyclic amides including amides of cyclohexane radical comprising carboxylic acid and amides with aromatic hydrocarbons, for example amides of benzoic acids.

In a preferred embodiment a hexosamine is transferred to a hexosamine by a glycosyltransferase, preferably galactosamine is transferred to galactosamine, most preferably the product GalNα3GalNβ4GlcNAc is formed, this product can be further modified to GalNAcα3GalNAcβGlcNAc or analogs according to the present invention by derivatization of aminogroups.

In a separate embodiment UDP-GalN is transferred by a α-galactosyltransferase, or α-GalNActransferase, preferably by α3-galactosyltransferase, to Galβ-terminal containing acceptor. The amine groups can be further derivatized to N-acetyl groups or analogs comprising derivatized aminen group. Preferably products of the process are for example GalNAcα3Galβ4GlcNAc, GalNα3Galβ4GlcNAc, GalNAcα3(Fucα2)Galβ4, GalNα(Fucα2)3Galβ4, GalNAcα3(Fucα2)Galβ3, GalNα(Fucα2)3Galβ3, GalNAcα3(Fucα2)Galβ4GlcNAc, GalNα(Fucα2)3Galβ4GlcNAc, which corresponds to human A/B-blood groups antigen terminal structures and analogs.

The present invention is further directed to novel carbohydrate substances according to the formula $GalN(Am)_{r1}α3(Fucα2)_{r2}Galβ3/4$    (V)

wherein r1 and r2 are independently 0 or 1, Am is a derivatization residue of amine group, with the provision that Am is not acetyl (Ac) or an imidogroup, preferably Am is carboxylic acid forming amide with the GalN such as formamide, propanoic acid amide, and other alkyl amides, and cyclic amides including amides of cyclohexane radical comprising carboxylic acid and amides with aromatic hydrocarbons, for example amides of benzoic acids. Acetyl group is not preferred for the analog substances as it is present in natural oligosaccharide sequences, bulky imidogroups such as phtalimido-group are not preferred because of the large size of the group which would change too much the conformation of the analog.

More preferred substances includes terminal oligosaccharide sequences
GalNα3Galβ4GlcNAc and GalNα3Galβ4Glc
GalNα3(Fucα2)Galβ4GlcNAc and GalNα(Fucα2)3Galβ4Glc
GalNAmα3(Fucα2)Galβ4GlcNAc and GalNAmα(Fucα2)3Galβ4Glc
GalNAmα3Galβ4GlcNAc and GalNAmα3Galβ4Glc.

And most preferred substances includes terminal oligosaccharide sequences
GalNAmα3(Fucα2)Galβ4GlcNAc and GalNAmα(Fucα2)3Galβ4Glc
GalNAmα3Galβ4GlcNAc and GalNAmα3Galβ4Glc.

The novel substances are especially useful for use as antigens and immunization. The rare and mostly non-natural or pathogenesis related structures are useful immunogens which can be used for inducing production of antibodies which also recognize related structures. Amine containing substances are also useful starting materials for production of further analogs, for testing as glycosidase substrates and/or inhibitors and testing as analogs of natural oligosaccharide sequences for binding of animal or plant lectins.

Present invention is specifically directed to the use of novel substances according to the present invention for immunization, and for screening of binding of lectins and antibodies. The present invention is especially directed to screening of specificities of antibodies binding to blood group antigens and screening related antibodies.

The present invention is specifically directed to the diagnostic and/or treatment of oral cancers including preferably cancer of larynx and leukemia-type cancers which express oligosaccharide sequences according to the present invention. The present invention is also specifically directed to the treatment according to the present invention for any type of cancer which has surface expression of the lacdiNAc structures according to the present invention. In another preferred embodiment the present invention is directed to the treatment of cancers from tissues which normally express and secrete proteins comprising lacdiNAc sequences, such tissues include glycoprotein hormone secreting tissues.

Glycolipid and carbohydrate nomenclature is according to recommendations by the IUPAC-IUB Commission on Biochemical Nomenclature (Carbohydr. Res. 1998, 322:167; Carbohydr. Res. 1997, 297:1; Eur. J. Biochem. 1998, 257:29).

It is assumed that Gal, Glc, GlcNAc, and NeuNAc are of the D-configuration, Fuc of the L-configuration, and that all monosaccharide units are in the pyranose form. Glucosamine is referred as GlcN and galactosamine as GalN. Glycosidic linkages are shown partly in shorter and partly in longer nomenclature, the linkages α3 and α6 of the NeuNAc-residues mean the same as α2-3 and α2-6, respectively, and β1-3, β1-4, and β1-6 can be shortened as β3, β4, and β6, respectively. Lactosamine or N-acetyllactosamine or Galβ3/4GlcNAc means either type one structure residue Galβ3GlcNAc or type two structure residue Galβ1-4GlcNAc, and sialic acid is N-acetylneuraminic acid or NeuNAc, Lac refers to lactose and Cer is ceramide. SA refers to sialic acid such as NeuNAc. The cancer associated disaccharide sequence according to the invention, GalNAcβ4GlcNAc, is referred as lacdiNAc or LacdiNAc.

The present invention is further illustrated in examples, which in no way are intended to limit the scope of the invention:

EXAMPLES

Example I

Methods for Analysis of MMP-9
Isolation of MMP-9

MMP-9 was isolated from U-937 cells by sequential CM-cellulose (CM-52) chromatography followed by DEAE/Red Sepharose chromatography (Saarinen et al, 1999).

4-Vinylpyridine Alkylation of MMP-9

MMP-9 was concentrated and desalted by reversed-phase chromatography (RP-HPLC) on a 2.1×150-mm Poros® R2 column by elution with a linear gradient of acetonitrile (3-100% in 15 min) in 0.1% trifluoroacetic acid. Chromatography was performed at a flow rate of 1 ml/min and elution was monitored by UV absorbance at 214 nm. The eluted MMP-9 was vacuum-dried and subjected to alkylation as follows: a sample was dissolved in 80 μl of 6M guadine hydrochloride, 2 mM EDTA, 0.5M Tris pH 7.5, reduced by addition of 5 μl of 0.6M DTT, and incubated for 20 minutes at room temperature. After reduction, 1 μl of 4-vinylpyridine was added, followed by alkylation for 15 minutes at room temperature.

The reaction was quenched by addition of 5 μl of 0.6M DTT. The alkylated MMP-9 was immediately desalted by RP-HPLC, as described above.

Trypsin Digestion 2.5 μg (100 pmol) of alkylated MMP-9 was vacuum-dried and dissolved in 40 μl of 50 mM ammonium bicarbonate buffer containing 1.66 ng/μl of trypsin (Promega sequencing grade). Digestion was performed overnight at 37 C.

Mass Spectrometry

MALDI:TOF MS was performed on a Biflex (Bruker Franzen Analytik) time of flight instrument equipped with a nitrogen laser operating at 337 m. The total MMP-9 N-glycans, as well as the results of the NDV sialidase reactions were analysed in the linear positive ion delayed extraction mode using 2,4,6-trihydroxyacetophenone (Fluka Chemie AG, 3 mg/ml in acetonitrile/20 mM aqueous diammonium citrate, 1:1, v/v) as the matrix. The *C perfringens* sialidase and the fucosidase treated glycans were analysed in the reflector positive ion delayed extraction mode using 2,5,-dihydrobenzoic acid (10 mg/ml) as the matrix. The spectra were externally calibrated with dextran 5000 (Fluka Chemie AG).

Electrospray ionization (ESI) mass spectra were collected using a Micromass Q-TOF hybrid quadrupole time-of-flight mass spectrometer (Micromass, UK). Ionization was accomplished by directing the LC eluent through a nanospray ion source equipped with a silica capillary needle 20 μm i.d., 10 μm tip opening, gold-coated from the distal end (New Objective Inc), operating at 2.2 kV.

Localization of Glycosylation Sites by Nanoflow LC/MS.

A sample of MMP-9 tryptic peptides (1 pmol) was separated by microbore reversed-phase HPLC on a 0.075×150 mm PepMap column (NAN75-15-03-C18-PM, LC Packings) by elution with a linear gradient of acetonitrile (4-40% in 30 min) in 0.1% formic acid. Chromatography was performed at a flow rate of 250 nl/min and the UV absorbance at 214 nm was recorded. LC was directly coupled to a Micromass Q-TOF mass spectrometer. The mass spectrometer was set to scan the HPLC eluent at both low and high cone settings to facilitate identification of the glycosylated components, as described previously (Carr et al., 1993). A low cone scan was acquired with a cone voltage of 35 V, scanning over a mass range of m/z 100 to 2500, thus providing a mass spectrum of the eluting components. A high cone scan was acquired with a cone voltage of 120 V, which applies a high collisional excitation potential to all ions during their entry into the mass spectrometer. This leads to collision-induced fragmentation of the entering ions prior to mass separation. During a high cone potential scan the mass spectrometer was set to scan from m/z 100 to 1000. Reconstituted chromatograms were then created for 204.1 (oxonium ion of HexNAc) and m/z 292.15 (oxonium ion of Neu5Ac) and m/z 366.1 (oxonium ion of Hex-HexNac), thus providing chromatograms selective for eluting glycopeptides.

Analysis of LacdiNAc Structures from Leukaemia Cells

To demonstrate abnormal expression of LacdiNAc sequence on cancer cells metalloproteinase-9 (MMP-9) was isolated from leukaemia cells (U-937), and N-glycosidic glycans were liberated with N-glycosidase F. The glycan fraction was analyzed with MALDI-TOF MS in trihyxroacetophenone matrix (FIG. 1A), which has been shown to cause negligible fragmentation of sialic acid residues. The assignment of the monosaccharide compositions as well as the proposed structures according to the subsequent glycosidase treatments are shown in Table 1. The relative abundances of the components are indicated as well, as oligosaccharide analysis in MALDI-TOF has been shown to be relatively quantitative. The most abundant glycan species was assigned to $[M+Na]^+$ of $(Hex)_5(HexNAc)_4(Fuc)_3$. Knowing the typical N-glycan structures, we tentatively assigned this structure as a trifucosylated diantennary complex-type glycan. Other major species were identified as sialylated, difucosylated diantennary complex-type glycan, and trifucosylated diantennary complex-type glycan carrying GalNAc instead of Gal as a terminal monosaccharide (so called LacdiNAc structure) in one antennae. These assignments were found to be correct, as shown by sequential glycosidase treatments. For comparison the matrix metalloproteinase MMP-9 structures in non-malignant white blood cells (leukocytes) has been determined, the protein did not contain lacdiNAc sequences (Rudd et al, 1999).

Figure 1B:
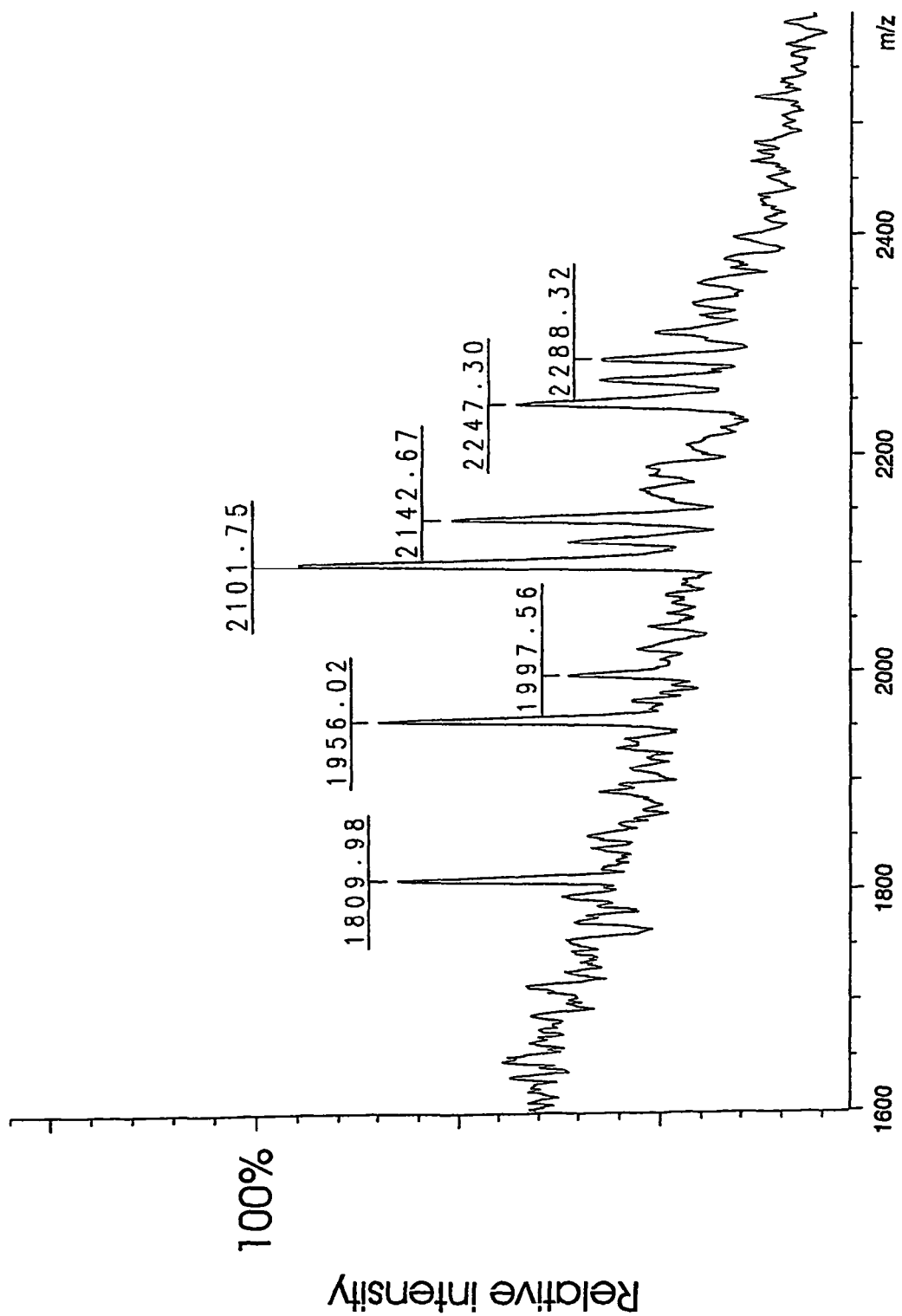
Figure 1C:
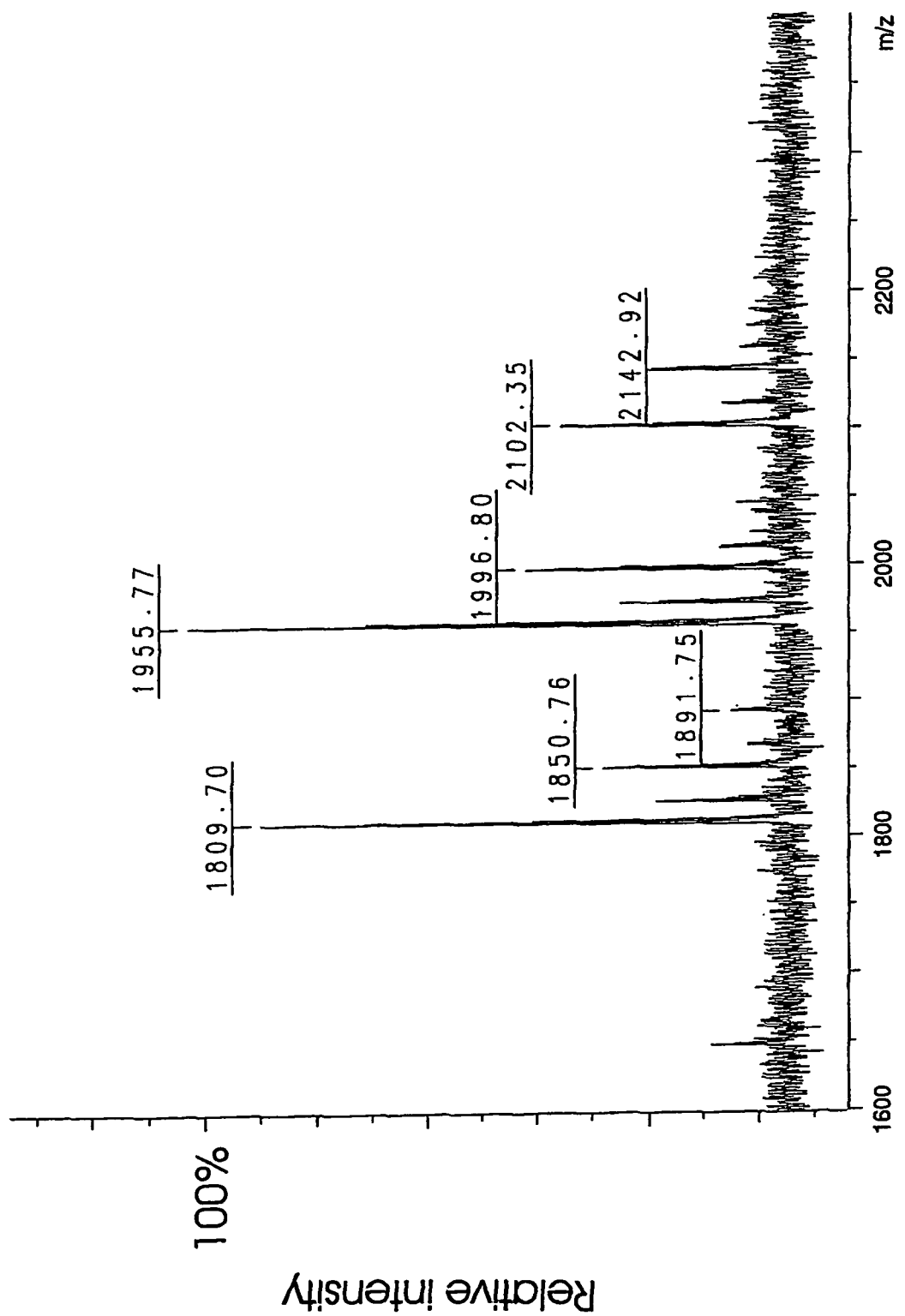
Figure 1D:
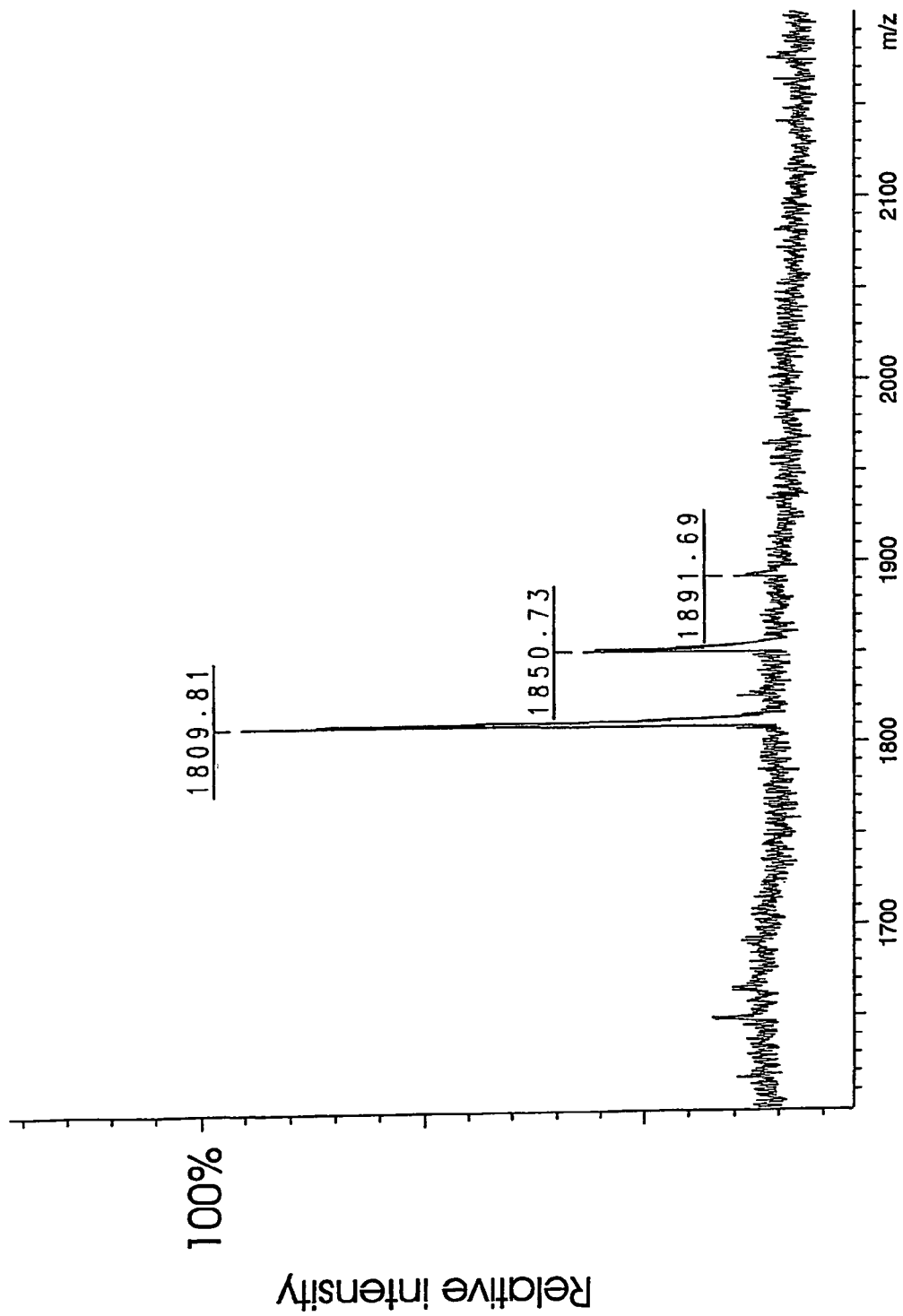

Structural characterization of the glycans was performed by sequential glycosidase treatments, which were monitored by MALDI-TOF MS. To distinguish the two plausible Neu5Ac linkages ($\alpha$2-3 vs. $\alpha$2-6), the glycan mixture was treated with NDV neuraminidase, an enzyme strictly specific for $\alpha$2-3neuraminic acid. Partial cleavage could be observed (FIG. 1B) that may arise from SA $\alpha$2-3GalNAc bond, which has been shown to resist the action of NDV sialidase. Other possibility is the presence of both $\alpha$2-3 and $\alpha$2-6 linked SA. Treatment of the N-glycan fraction with a broad specificity neuraminidase (*Clostridium perfingens*) resulted in following changes (FIG. 1C): Signals at m/z 2247.3, 2287.9, and 2392.3 disappeared, and signals appeared at m/z 1809.70, 1850.78, 1891.75, 1955.77, and 1996.79. The results indicate the presence of differentially fucosylated forms of normal biantennary N-glycans, biantennary N-glycans carrying LacdiNAc structure (GalNAc$\beta$1-4GlcNAc) in one of the antennae, and a minor amount of N-glycans carrying LacdiNAc structure in both of the antennae. Treatment of the sample by Almond meal $\alpha$1-3(4)fucosidase (which removes the $\alpha$1-3(4) linked fucose residues from the antennae, but does not cleave the $\alpha$1-6 linked fucose residue from the N-glycan core) led to appearance of signals at 1809.80, 1850.78, and 1891.84 (67%, 27% and 6% of intensity). These results indicate that approximately 30% of the glycans carry LacdiNAc sequence in either one or both of the antennae. This result is well in accordance with the LC-ESI MS data presented below.

Figure 2:
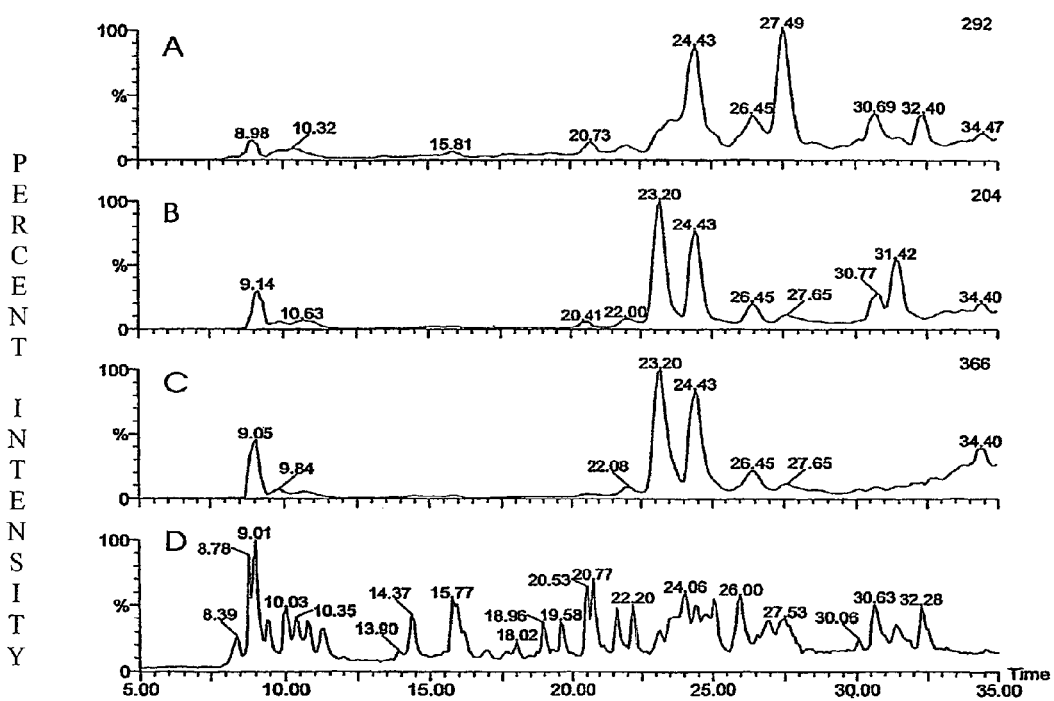
FIG. 2. LC-ESI MS analysis of tryptic digest of MMP-9. Panel A) shows total ion chromatogram of eluting peptides; Panel B) shows extracted ion chromatogram of m/z 0.204.1 (Oxonium ion of Hex); Panel C) shows extracted ion chromatogram of m/z 292.1 (Oxonium ion of SA); and Panel D) shows extracted ion chromatogram of m/z 366.1 (Oxonium ion of Hex-HexNac). Panels B, C and D show putative glycopeptides.

MMP-9 was isolated from U-937 cells, alkylated, and digested with trypsin. To identify the glycopeptides, we conducted an LC/MS analysis of tryptic peptides from MMP-9, using stepped cone voltages to obtain both the total ion chromatogram (FIG. 2A) and chromatograms showing potential glycopeptides (FIGS. 2B, C and D). It should be noted that in the chromatography setup used in this study (i.e. PepMap media run in 0.1% formic acid-acetonitrile), the separation of glycopeptides is affected by both the peptide moiety and the glycan moiety. In the more commonly used trifluoroacetic acid-acetonitrile system, the separation of the glycopeptides is dominated by the peptide moiety alone. This leads to elution of the glycopeptides as two major peaks eluting at 23.1 and 24.3 minutes.

Figure 3A:
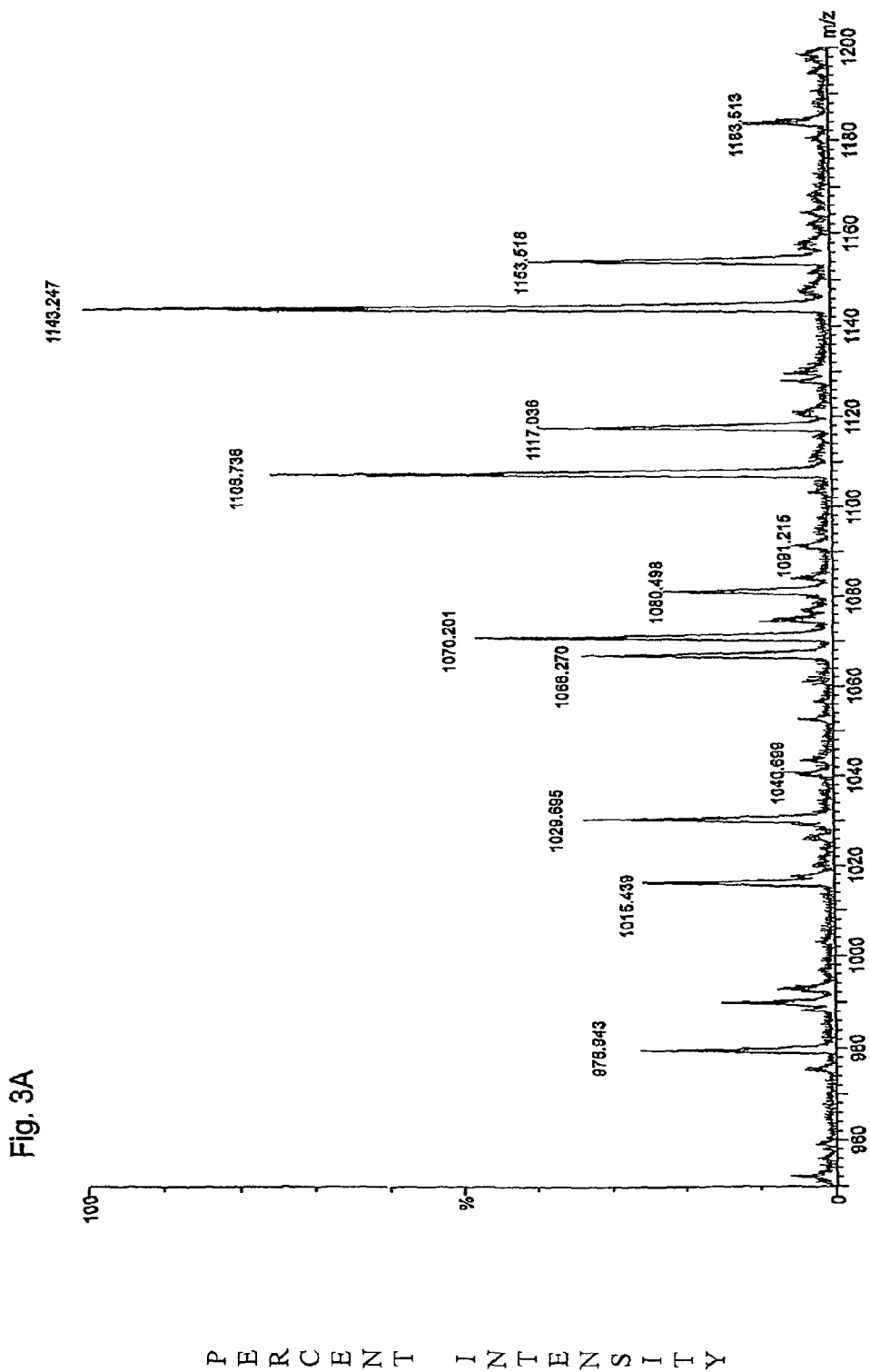
FIGS. 3A and 3B. LC/MS analysis of tryptic peptides from MMP-9. (3A) Mass spectrum corresponding to glycopeptides eluting at 23.1 minutes, (3B) mass spectrum corresponding to glycopeptides eluting at 24.3 minutes.
Figure 3B:
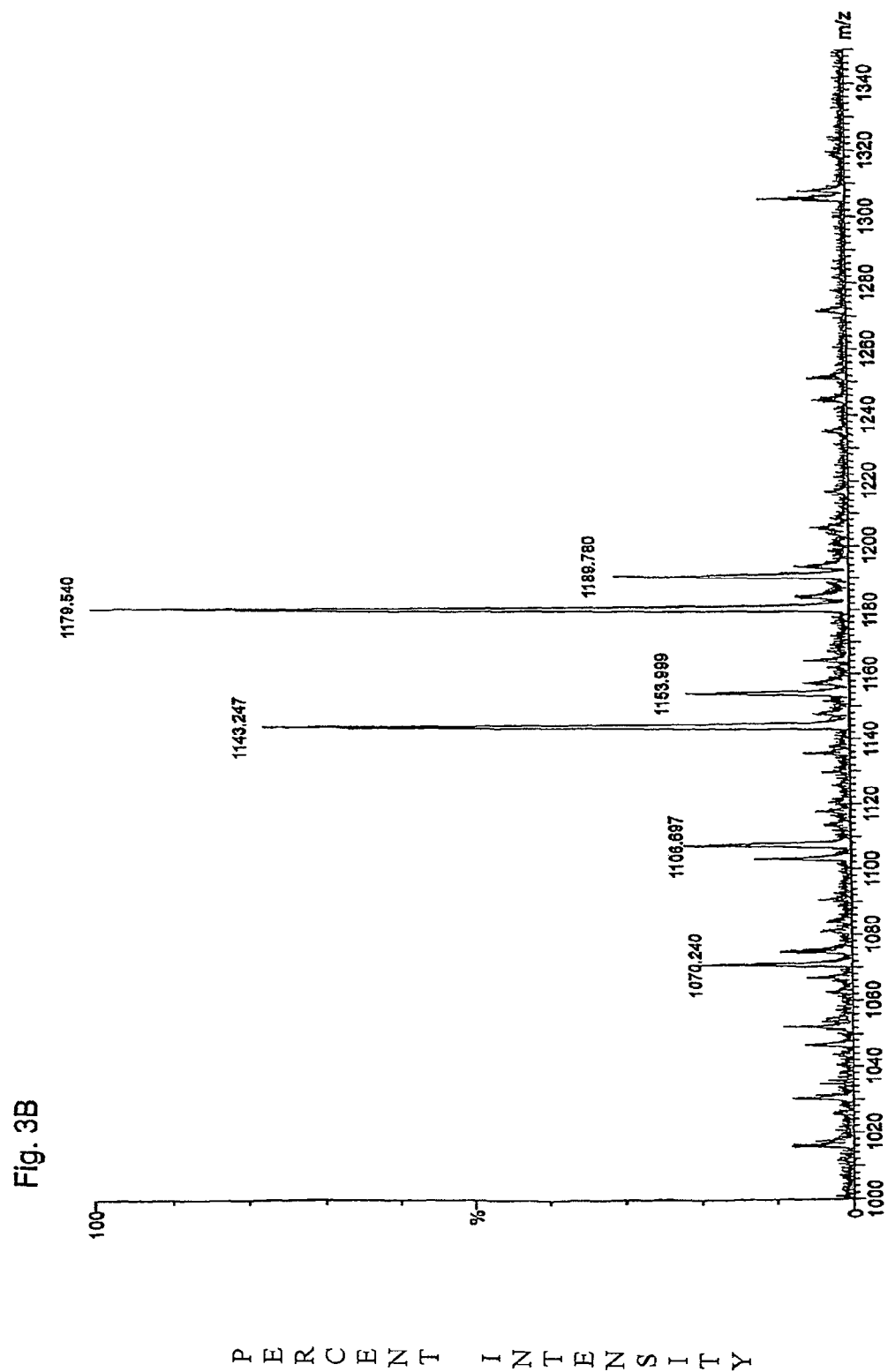
Figure 4A:
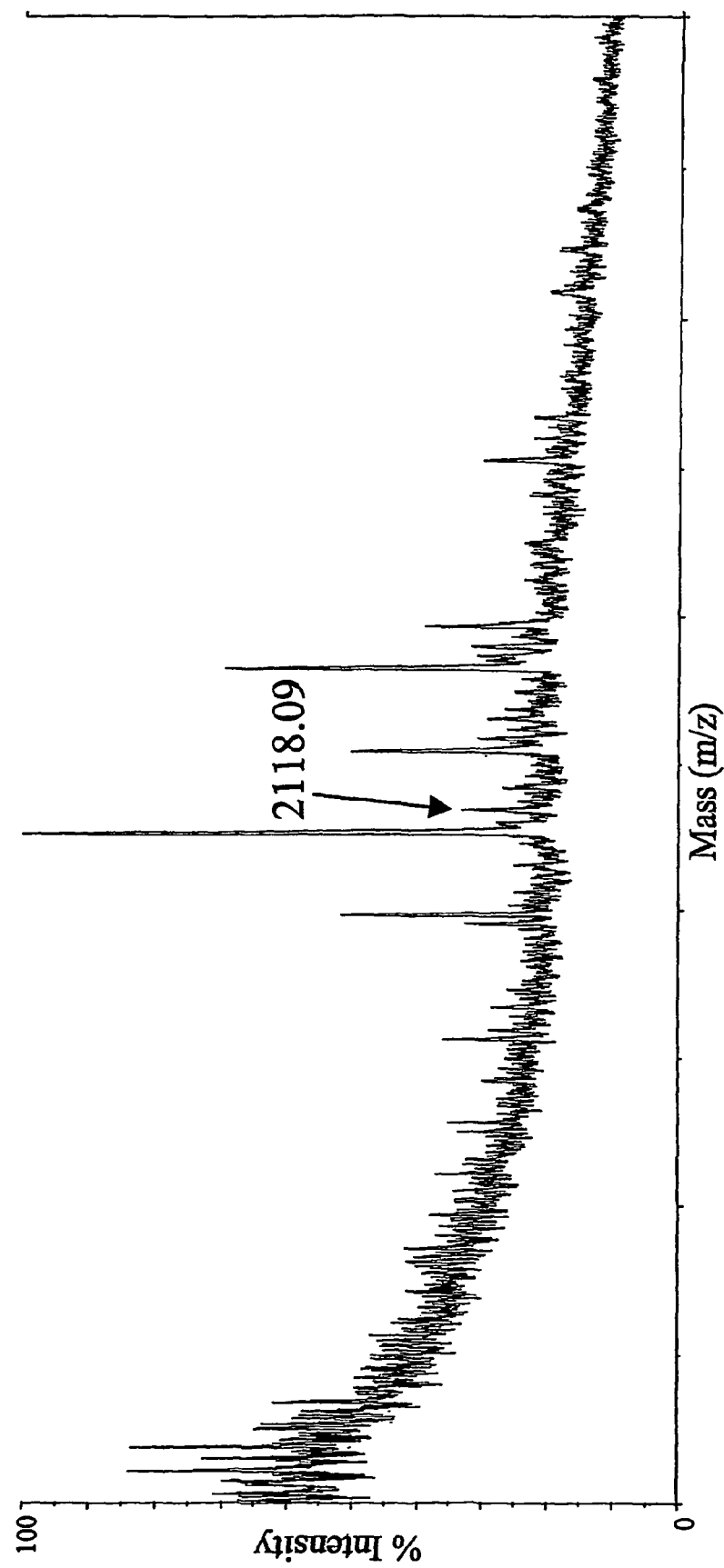
FIG. 4A. Negative ion linear mode MALDI-TOF mass spectrum of larynx cancer sample sialylated glycans.
Figure 4B:
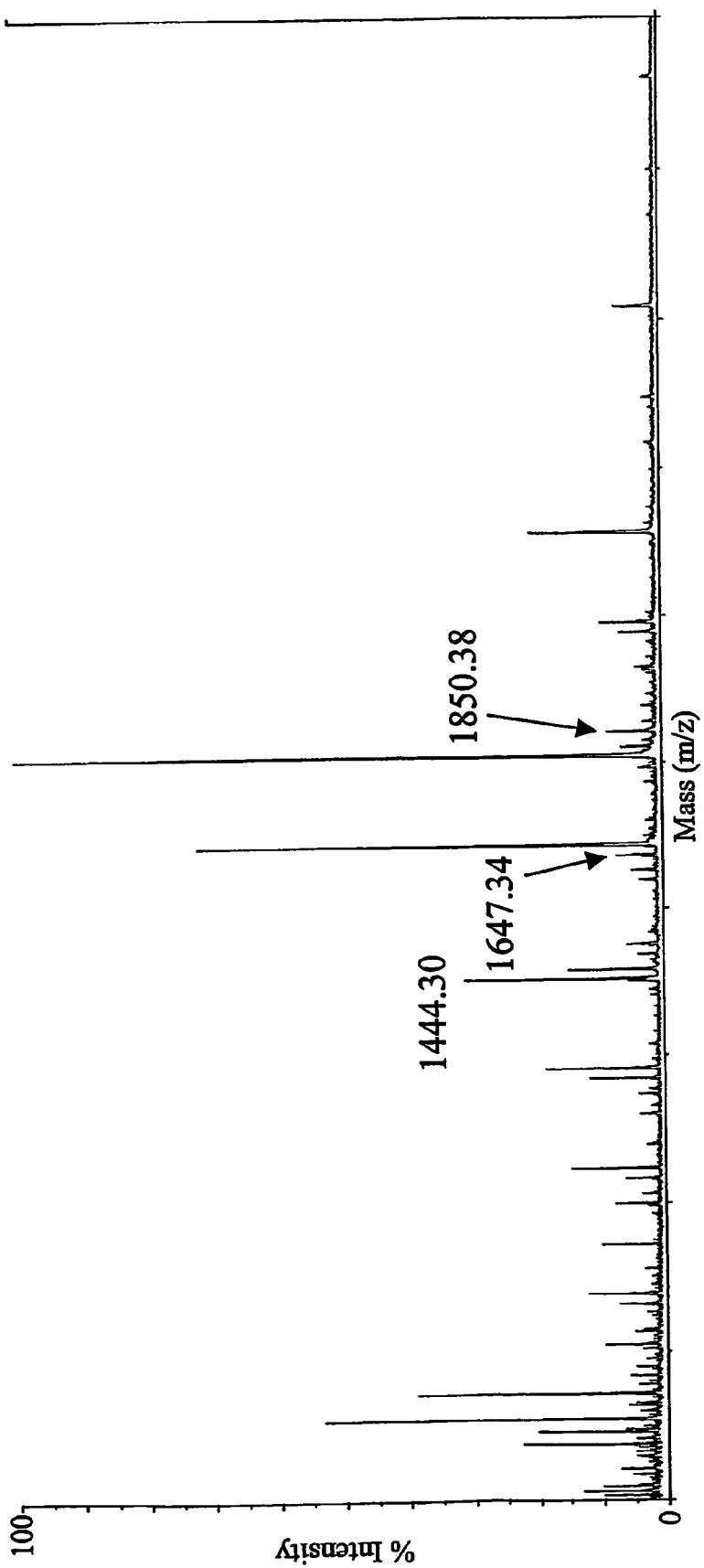
FIG. 4B. Positive ion reflector mode MALDI-TOF mass spectrum of larynx cancer sample sialylated glycans after *A. ureafaciens* sialidase and *S. pneumoniae* β-N-acetylglucosaminidase digestions.
Figure 4C:
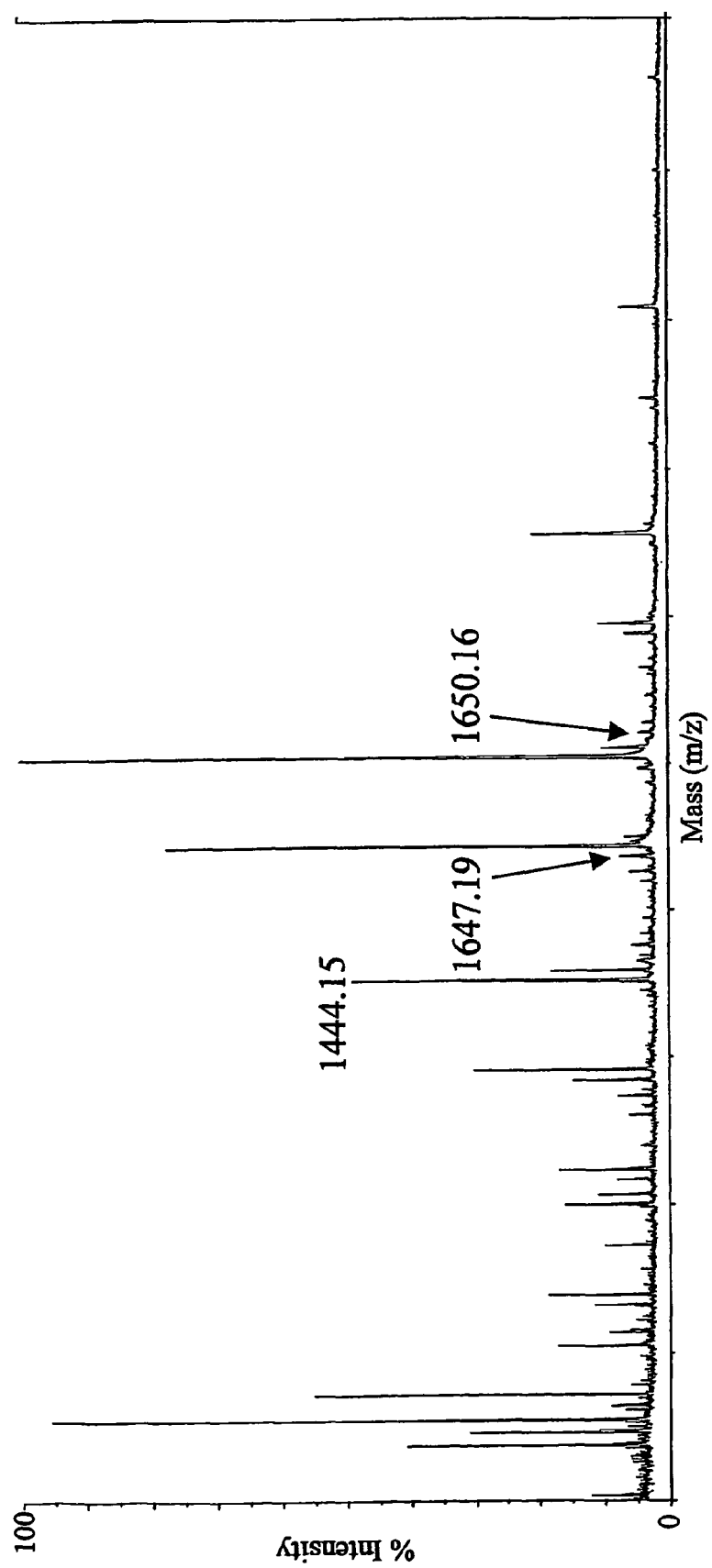
FIG. 4C. Positive ion reflector mode MALDI-TOF mass spectrum of larynx cancer sample sialylated glycans after *A. ureafaciens* sialidase, *S. pneumoniae* β-N-acetylglucosaminidase, and Jack bean β-N-acetylhexosaminidase digestions.

The mass spectrum of the material eluting at 23.1 min is presented in FIG. 3A, and shows signals which could all be assigned to glycosylated peptide $Trp^{116}$-$Arg^{134}$, carrying complex-type glycans (see Table 1). The most intense ion in this spectrum at m/z 1143.49 is assigned to $[M+4H]^{4+}$ of $Trp^{116}$-$Arg^{134}$, carrying $(Hex)_5(HexNAc)_4(Fuc)_3$. The mass spectrum of the material eluting at 24.3 min is presented in FIG. 3B. The most intense ion in this spectrum at m/z 1179.54 is assigned to $[M+4H]^{4+}$ of $Trp^{116}$-$Arg^{134}$, carrying $(Hex)_5(HexNAc)_4(Fuc)_2(SA)_1$.

The present invention shows that U-937-cell derived MMP-9 carries LacdiNAc structures in large fraction (approximately 30%) of its N-glycans. The presence of LacdiNAc structures was verified by two independent methods, namely MALDI-TOF analysis of liberated N-glycans as well as LC-ESI MS of intact glycopeptides. The assignments of the structures were further confirmed by sequential glycosidase treatments. The methods used in this study have been verified by several approaches using both known natural structures as well as synthetic oligosaccharides.

Sialylated N-glycans that contain LacdiNAc sequences from larynx cancer. Human melanoma cell (RPMI-7932 and RPMI-7951) membrane protein N-glycans that contain LacdiNAc, sialyl-LacdiNAc, and fucosyl-LacdiNAc sequences.

Example II

Analysis of Solid Tumor and Melanoma Cell Membranes

Cancer sample material. The larynx cancer sample was a formalin-fixed tumor specimen collected during a surgical operation. Prior to glycan isolation, proteins were enriched by chloroform-methanol extraction essentially as described in (Manzi et al., 2000). Quantitative extraction of glycoproteins was confirmed by radioactively labelled glycoprotein standards (not shown).

Isolation of glycans from chloroform-methanol extracted proteins. Glycans were detached from sample glycoproteins by non-reductive $\beta$-elimination and purified by chromatographic methods.

Isolation of human melanoma cell membrane proteins. Human melanoma cells (RPMI-7932 and RPMI-7951) were washed with phosphate buffered saline (PBS) at room temperature, scraped off from cell culture dishes, and collected by centrifugation. Thereafter, the purification process continued at +0-+4° C. The cells were incubated in hypotonic buffer, 25 mM Tris-HCl pH 8.5, broken by homogenisation, and brought back to isotonic buffer by the addition of NaCl to 150 mM. The nuclei were separated from the bulk of cell membranes by low-speed centrifugation, which was monitored by microscopy. The supernatant, containing the membranes and cytosolic material, was centrifuged at 40,000 g. The pellet (the membrane preparation) was homogenized in detergent buffer containing 25 mM Tris-HCl pH 8.5, 150 mM NaCl, and 1% (w/v) Triton X-100. After incubation, the preparate was centrifuged at 100,000 g and the supernatant, containing the detergent extracted membrane proteins, was collected. Buffer salts and the detergent were removed by cold acetone precipitation as in (Verostek et al., 2000).

Isolation of membrane protein N-glycans. N-glycans were detached from membrane glycoproteins with *Chryseobacterium meningosepticum* N-glycosidase F (Calbiochem, USA) essentially as in (Nyman et al., 1998) and purified essentially as in (Verostek et al., 2000; Packer et al., 1998). N-glycans from RPMI-7951 cells were additionally passed through columns of 1) AG-50W strong cation exchange material and 2) $C_{18}$ silica in water, whereas N-glycans from RPMI-7932 cells were not. The N-glycans were separated into sialylated and non-sialylated fractions with graphitised carbon columns essentially as in (Packer et al., 1998).

MALDI-TOF MS. MALDI-TOF mass spectrometry was performed with a Voyager-DE STR BioSpectrometry Workstation, essentially as in (Saarinen et al., 1999; Papac et al., 1996; Harvey, 1993).

Exoglycosidase digestions. All exoglycosidase reactions were performed essentially as described in (Nyman et al., 1998; Saarinen et al., 1999) and analysed by MALDI-TOF MS. The enzymes and their specific control reactions with characterised oligosaccharides were: *Arthrobacter ureafaciens* sialidase (recombinant, *E. coli*; Glyko, UK) digested both Neu5Acα2-3Galβ1-4GlcNAc-R and Neu5Acα2-6Galβ1-4GlcNAc-R in oligosaccharides; β-N-acetylglucosaminidase (*Streptococcus pneumoniae*, recombinant, *E. coli*; Calbiochem, USA) digested GlcNAcβ1-6Gal-R but not GalNAcβ1-4GlcNAcβ1-3/6Gal-R; β-N-acetylhexosanini-dase (Jack bean; Calbiochem, USA) digested both GlcNAcβ1-6Gal-R and GalNAcβ1-4GlcNAcβ1-3/6Gal-R; α1,3/4-fucosidase (*Xanthomonas* sp.; Calbiochem, USA) digested Galβ1-4(Fucα1-3)GlcNAc-R but not Fucα1-2Galβ1-3GlcNAc-R Control digestions were performed in parallel and analysed similarly to the analytical exoglycosidase reactions.

Results

LacdiNAc containing sialylated N-glycans from larynx cancer samples. The sialylated glycans from larynx cancer samples were effectively desialylated with *Arthrobacter ureafaciens* sialidase. Desialylation was monitored by MALDI-TOF MS (not shown). The desialylated glycans were first digested with β-N-acetylglucosaminidase at enzyme concentrations that specifically hydrolyse terminal β-GlcNAc residues but not β-GalNAc residues. The further addition of β-N-acetylhexosaminidase removed 2 HexNAc residues from one of the N-glycans, indicating the presence of a GalNAcβ1-4GlcNAc sequence, which is resistant to the action of β-N-acetylglucosaminidase but is completely digested with β-N-acetylhexosaminidase. Upon β-N-acetylhexosaminidase digestion, the relative signal intensity of a peak at m/z 1850.38/1850.16, corresponding to the ion $[Hex_4HexNAc_5Fuc_1+Na]^+$ (calc. m/z 1850.67), was significantly decreased. Simultaneously, the relative signal intensity of a peak at m/z 1444.30/1444.15, corresponding to the ion $[Hex_4HexNAc_3Fuc_1+Na]^+$ (calc. m/z 1444.51), was increased, while there was no increase in the relative signal intensity of the incompletely digested form at m/z 1647.34/1647.19, corresponding to the ion $[Hex_4HexNAc_4Fuc_1+Na]^+$ (calc. m/z 1647.59). The one observed peak corresponding to a sialylated form of the LacdiNAc containing N-glycan in question, namely the ion at m/z 2118.09 $([NeuAc_1Hex_4HexNAc_5Fuc_1-H]^-$; calc. m/z 2118.93), contains only one sialic acid residue. However, the present data cannot exclude the presence of differently sialylated forms in the original sample. Importantly, no evidence of LacdiNAc containing glycans could be obtained in similarly analysed samples from many healthy tissues.

RPMI-7932 and RPMI-7951 human melanoma cell membrane protein desialylated N-glycans. The sialylated N-glycans, comprising to membrane-associated sialylated N-glycans, were effectively desialylated with *Arthrobacter ureafaciens* sialidase. Desialylation was monitored by MALDI-TOF MS (data not shown). The desialylated N-glycans were first digested with β-N-acetylglucosaminidase at enzyme concentrations that specifically hydrolyse terminal β-GlcNAc residues but not β-GalNAc residues. The further addition of β-N-acetylhexosaminidase removed HexNAc residues from some of the N-glycans. Below are the examples of the β-N-acetylhexosaminidase sensitive and β-N-acetylglucosaminidase insensitive structures, from which the enzyme removed exclusively either 2 or 4 HexNAc residues at a time. Taken together, this indicates that these structures contain GalNAcβ1-4GlcNAc sequences, which are resistant to the action of β-N-acetylglucosaminidase but are completely digested with β-N-acetylhexosamidase.

Figure 5:
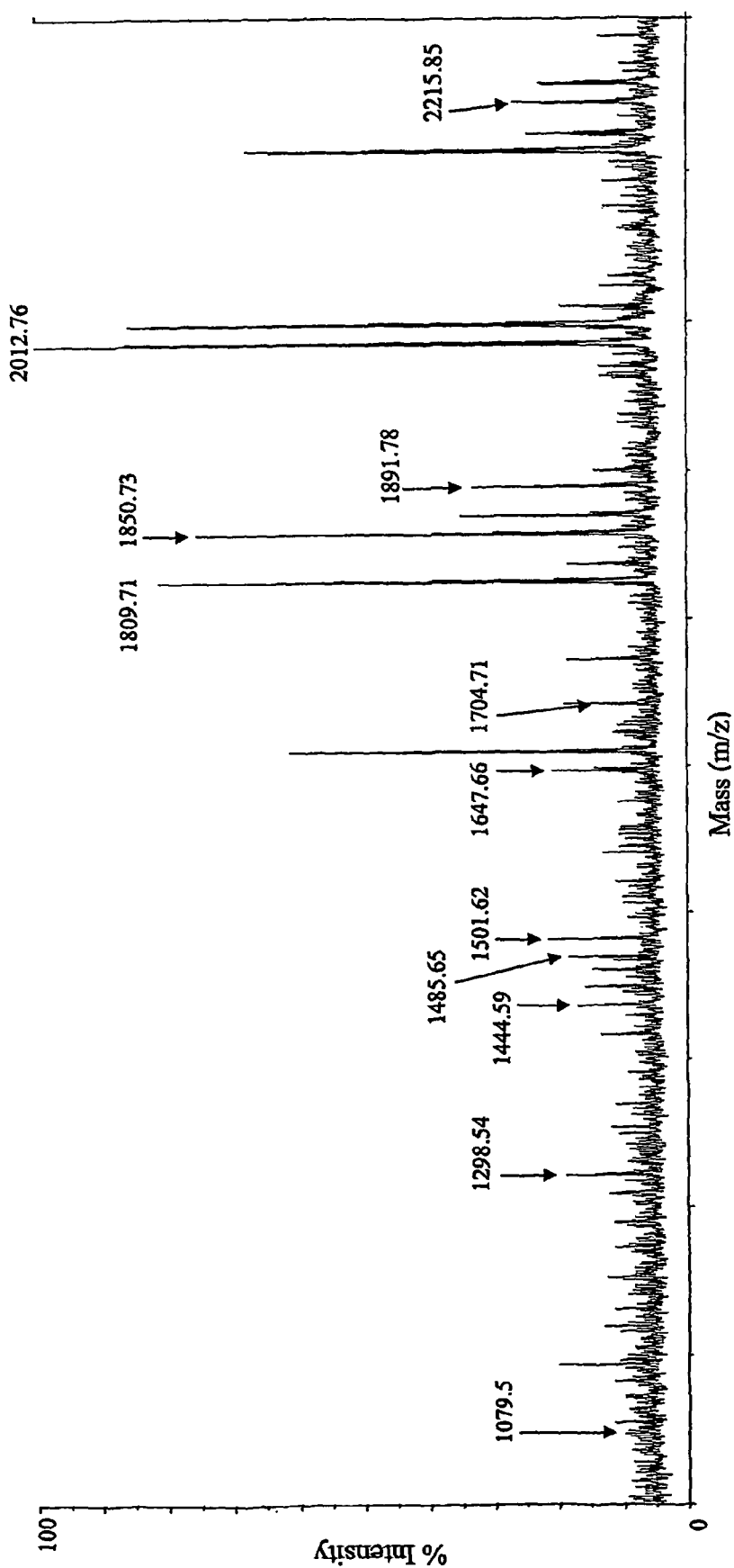
FIG. 5. Positive ion reflector mode MALDI-TOF mass spectrum of RPMI-7932 melanoma cell line membrane protein sialylated N-glycans after *A. ureafaciens* sialidase and *S. pneumoniae* β-N-acetylglucosaminidase digestions.
Figure 6:
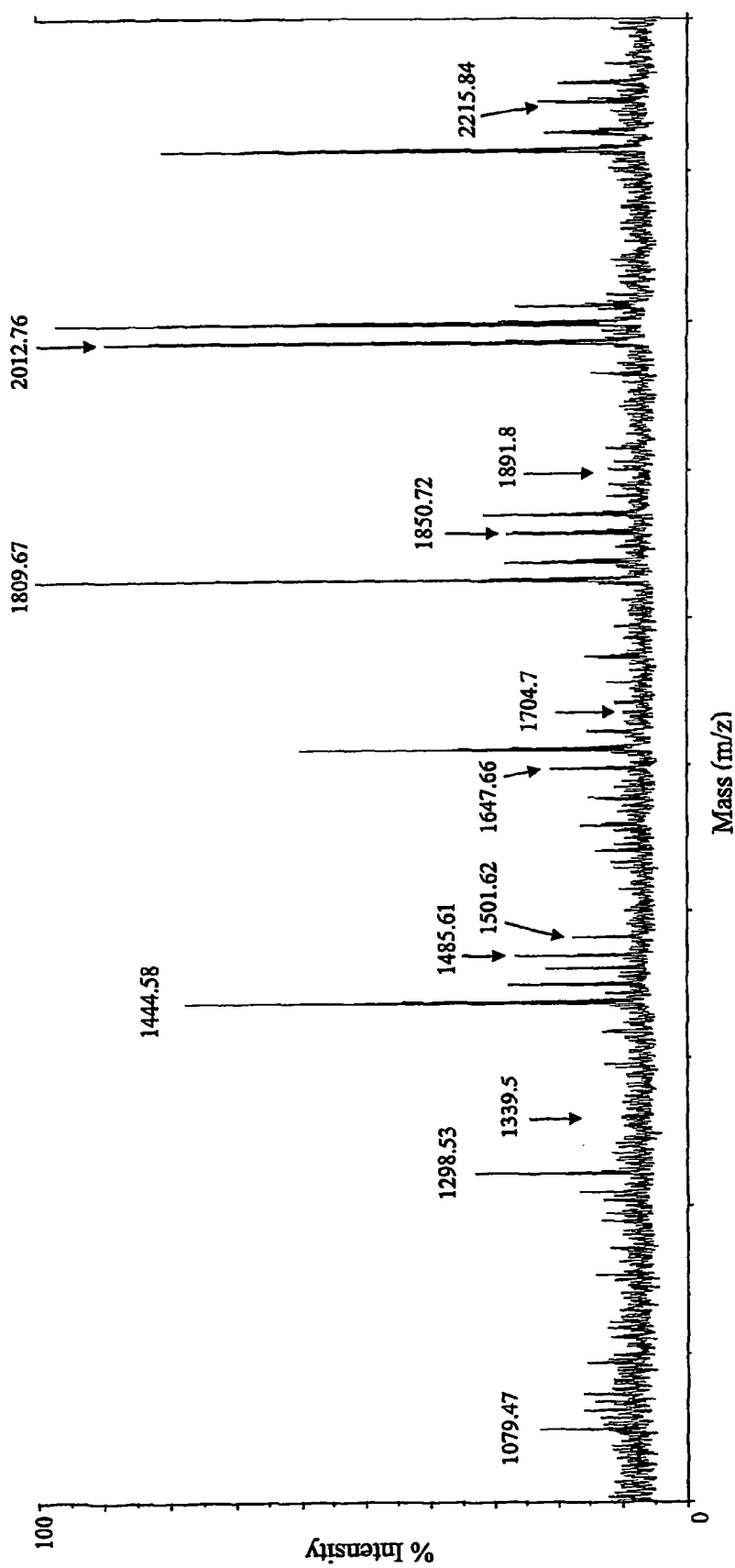
FIG. 6. Positive ion reflector mode MALDI-TOF mass spectrum of RPMI-7932 melanoma cell line membrane protein sialylated N-glycans after *A. ureafaciens* sialidase, *S. pneumoniae* β-N-acetylglucosaminidase, and Jack bean β-N-acetylhexosaminidase digestions.
Figure 7:
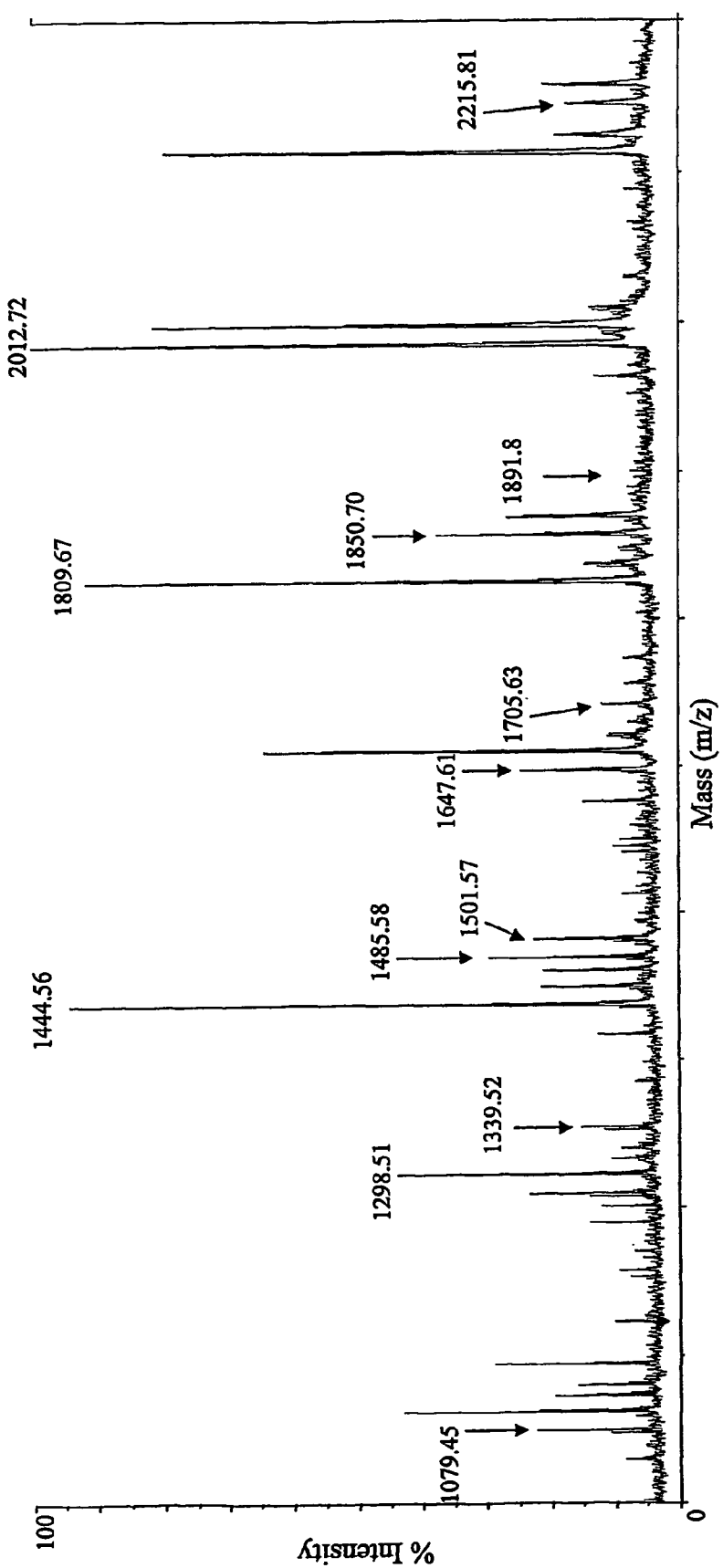
FIG. 7. Positive ion reflector mode MALDI-TOF mass spectrum of RPMI-7932 melanoma cell line membrane protein sialylated N-glycans after *A. ureafaciens* sialidase, Jack bean β-N-acetylhexosaminidase, and *Xanthomonas* sp. α1,3/4-fucosidase digestions.

LacdiNAc Containing N-Glycans from RPMI-7932 Human Melanoma Cell Membrane Proteins (FIG. 5.-7.):

A. Upon β-N-acetylhexosaminidase digestion, a peak at m/z 1704.71, corresponding to the ion $[Hex_4HexNAc_5+Na]^+$ (calc. m/z 1704.61), was transformed into a peak at m/z 1298.53, corresponding to the ion $[Hex_4HexNAc_3+Na]^+$ (calc. m/z 1298.45), while there was no increase in the relative signal intensity of the incompletely digested form at m/z 1501.62, corresponding to the ion $[Hex_4HexNAc_4+Na]^+$ (calc. m/z 1501.53).

B. Upon β-N-acetylhexosaminidase digestion, the relative signal intensity of a peak at m/z 1850.73/1850.72, corresponding to the ion $[Hex_4HexNAc_5Fuc_1+Na]^+$ (calc. m/z 1850.67), was significantly decreased. Simultaneously, the relative signal intensity of a peak at m/z 1444.59/1444.58, corresponding to the ion $[Hex_4HexNAc_3Fuc_1+Na]^+$ (calc. m/z 1444.51), was significantly increased, while there was no increase in the relative signal intensity of the incompletely digested form at m/z 1647.66, corresponding to the ion $[Hex_4HexNAc_4Fuc_1+Na]^+$ (calc. m/z 1647.59).

C. Upon β-N-acetylhexosaminidase digestion, a peak at m/z 1891.78, corresponding to the ion $[Hex_3HexNAc_6Fuc_1+Na]^+$ (calc. m/z 1891.69), was completely transformed into peaks at m/z 1079.47, corresponding to the ion $[Hex_3HexNAc_2Fuc_1+Na]^+$ (calc. m/z 1079.38), and m/z 1485.65/1485.61, corresponding to the ion $[Hex_3HexNAc_4Fuc_1+Na]^+$ (calc. m/z 1485.53), while no evidence could be found of the possible incompletely digested forms at calc. m/z 1688.61 $[Hex_3HexNAc_5Fuc_1+Na]^+$ or calc. m/z 1282.45 $[Hex_3HexNAc_3Fuc_1+Na]^+$. Upon α1,3/4-fucosidase digestion, the peak at m/z 1485.61 was partly transformed into a peak at 1339.52, corresponding to the ion $[Hex_3HexNAc_4+Na]^+$ (calc. m/z 1339.48).

D. Upon β-N-acetylhexosaminidase digestion, the relative signal intensity of a peak at m/z 2215.85/2215.84, corresponding to the ion $[Hex_5HexNAc_6Fuc_1+Na]^+$ (calc. m/z 2215.80), was significantly decreased. Simultaneously, the relative signal intensity of a peak at m/z 1809.71/1809.67, corresponding to the ion $[Hex_5HexNAc_4Fuc_1+Na]^+$ (calc. m/z 1809.64), was significantly increased, while there was no increase in the relative signal intensity of the possible incompletely digested form at m/z 2012.76, corresponding to the ion $[Hex_5HexNAc_5Fuc_1+Na]^+$ (calc. m/z 2012.72).

Figure 8:
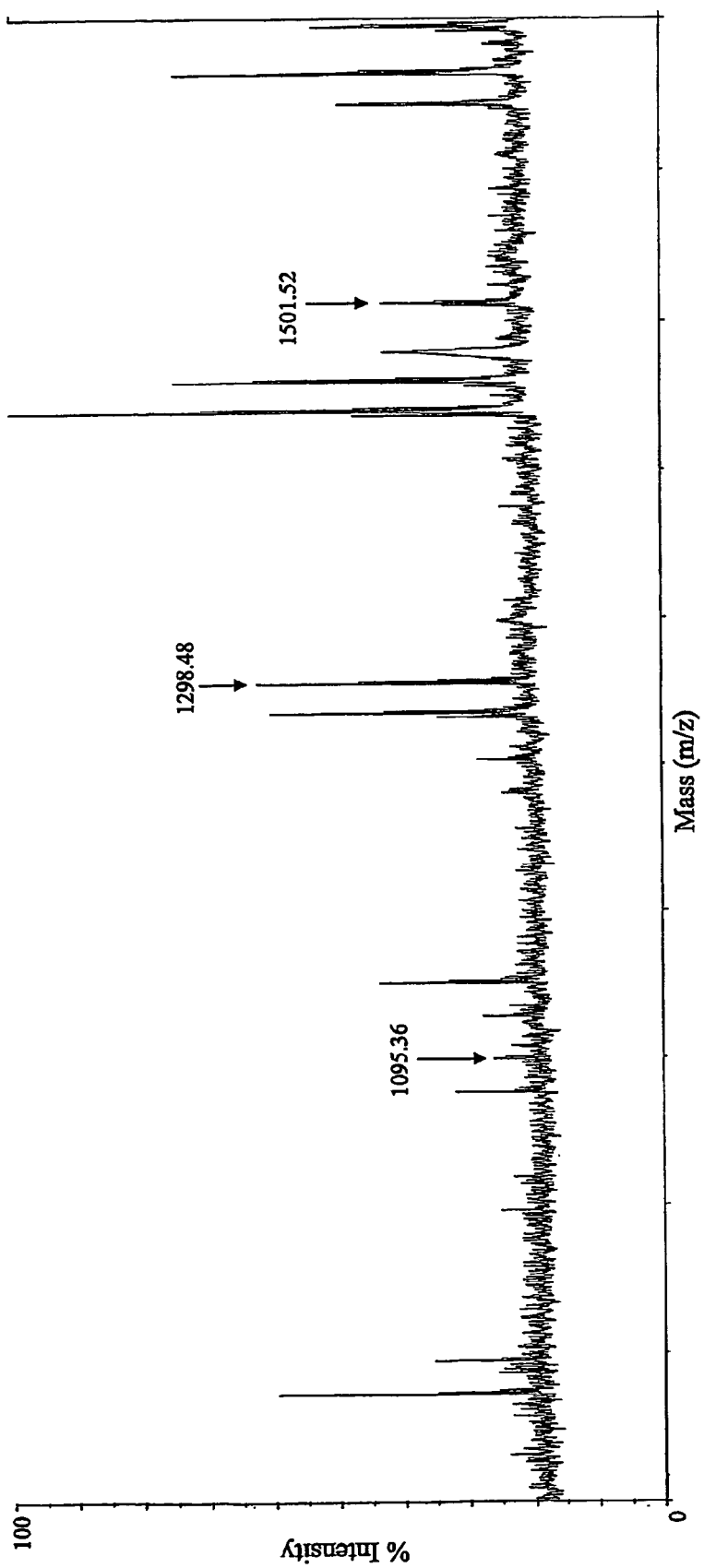
FIG. 8. Positive ion reflector mode MALDI-TOF mass spectrum of RPMI-7951 melanoma cell line membrane protein sialylated N-glycans after *A. ureafaciens* sialidase and *S. pneumoniae* β-N-acetylglucosaminidase digestions.
Figure 9:
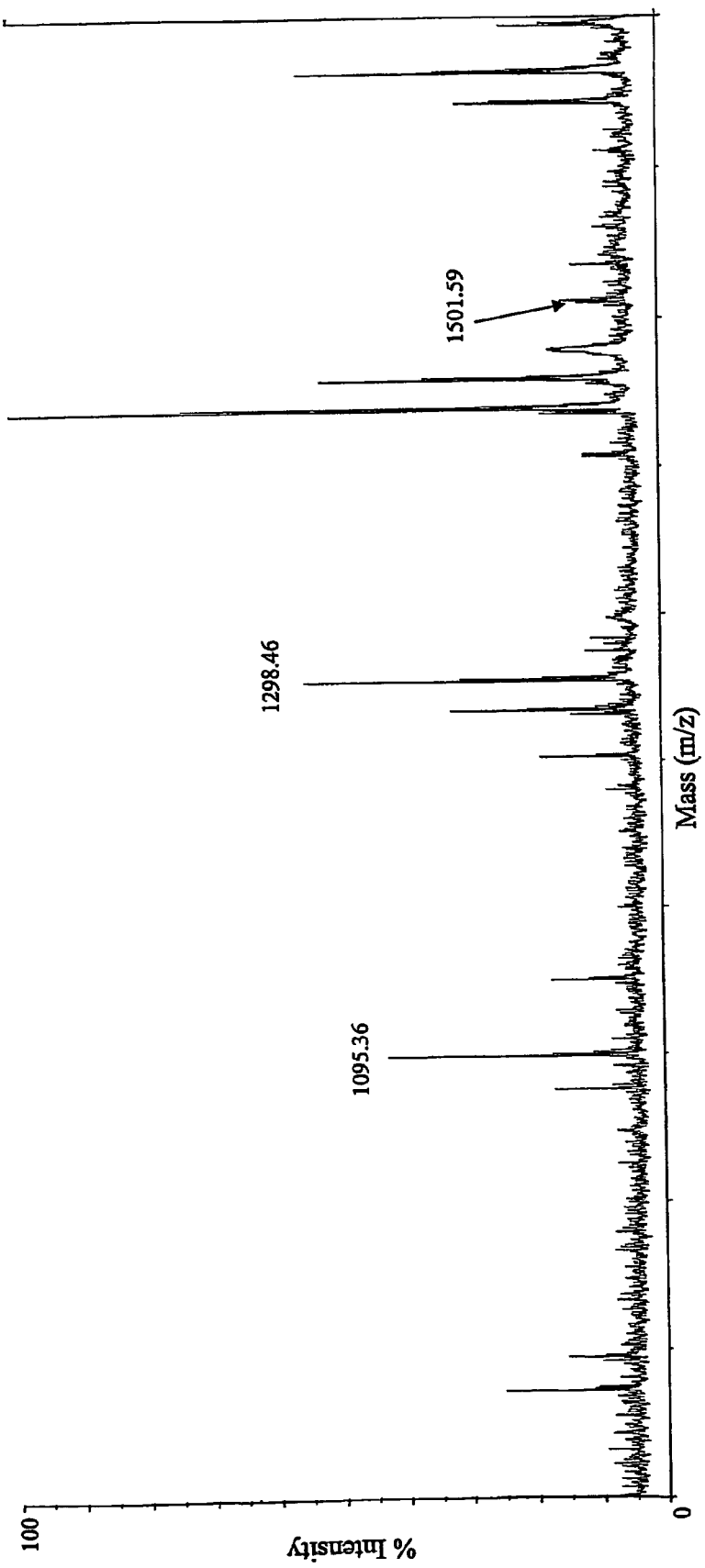
FIG. 9. Positive ion reflector mode MALDI-TOF mass spectrum of RPMI-7951 melanoma cell line membrane protein sialylated N-glycans after *A. ureafaciens* sialidase, *S. pneumoniae* β-N-acetylglucosaminidase, and Jack bean β-N-acetylhexosaminidase digestions.

LacdiNAc Containing N-Glycan from RPMI-7932 Human Melanoma Cell Line Membrane Proteins (FIG. 8.-9.):

E. Upon β-hexosaminidase digestion, a peak at m/z 1501.52, corresponding to the ion [Hex$_4$HexNAc$_4$+Na]$^+$ (calc. m/z 1501.53), was transformed into a peak at m/z 1095.36, corresponding to the ion [Hex$_4$HexNAc$_2$+Na]$^+$ (calc. m/z 1095.37), while there was no significant increase in the relative signal intensity of the incompletely digested form at m/z 1298.48/1298.46, corresponding to the ion [Hex$_4$HexNAc$_3$+Na]$^+$ (calc. m/z 1298.45).

Conclusions

The present results indicate that human cancerous tissue contains glycoproteins that carry LacdiNAc sequences. More specifically, the results show that a LacdiNAc containing a sialylated N-glycan, NeuAc$_1$Hex$_4$HexNAc$_5$Fuc$_1$, is expressed on glycoproteins of a larynx cancer tumor specimen. Furthermore, the present results suggest the presence of several LacdiNAc, sialyl-LacdiNAc, and/or fucosyl-LacdiNAc containing structures among the sialylated N-glycans of RPMI-7932 melanoma cell membrane proteins, and the presence of a sialyl-LacdiNAc containing N-glycan among the sialylated N-glycans of RPMI-7951 melanoma cell membrane proteins. In structure C. of RPMI-7932 melanoma cell line membrane protein desialylated N-glycans, namely Hex$_3$HexNAc$_6$Fuc$_1$, at least one of the LacdiNAc units is originally sialylated, as the N-glycans were obtained through *Arthrobacter ureafaciens* sialidase digestion from isolated sialylated N-glycans. Similarly, in structure C. of RPMI-7932 melanoma cell line membrane protein sialylated N-glycans, at least one of the two LacdiNAc sequences must be β-linked to one of the α-mannoses of the N-glycan core. Furthermore, α1,3/4-fucosidase digestion revealed the presence of α1,3-fucosylated LacdiNAc sequences in structure C. of RPMI-7932 melanoma cell line membrane protein sialylated N-glycans. In the other structures, the presence of Hex-HexNAc sequences prevents these structure assignments. The monosaccharide composition of structure E. of RPMI-7951 melanoma cell line membrane protein desialylated N-glycans, Hex$_4$HexNAc$_4$, suggests the presence of a hybrid N-glycan that has a sialyl-LacdiNAc sequence on a Man$_4$GlcNAc$_2$ N-glycan core.

Example III

Anti-LacdiNAc Antibodies that Recognize GalNAcβ1-4GlcNAc Sequences on Cancer Cells and Glycoconjugates, and Immunogenic Oligosaccharide Conjugates Used to Produce and Characterize Them Antibodies. Anti-LacdiNAc antibodies are produced by immunogenic LacdiNAc conjugates by standard methods in experimental animal immunology or screening antibody libraries by phage display or other methods known in the art. The used possibly monoclonal antibodies are shown to be specific towards LacdiNAc by ELISA with specific oligosaccharide or oligosaccharide conjugate coated ELISA plates, or any other suitable method that utilizes recognition of specific oligosaccharides or their conjugates. Antibodies that bind to the LacdiNAc antigen without binding to the respective LacNAc analog, are suitable for theit intended use. The specific pairs of a LacdiNAc antigen and a LacNAc control antigen, suitable for conjugation as neoglycoproteins or other immunogenic conjugates, are for example as follows: GalNAcβ14GlcNAcβ1-3Galβ1-R and Galβ1-4GlcNAcβ1-3Galβ1-R, GalNAcβ4GlcNAcβ1-6Galβ1-R and Galβ1-4GlcNAcβ1-6Galβ1-R, GalNAcβ1-4GlcNAcβ1-3GalNAcα1-R and Galβ1-4GlcNAcβ1-3GalNAcα1-R, GalNAcβ1-4GlcNAcβ1-6GalNAcα1-R and Galβ1-4GlcNAcβ1-6GalNAcα1R, GalNAcβ1-4GlcNAcβ1-2Manα1-R and Galβ1-4GlcNAcβ1-2Manα1-R, GalNAcβ1-4GlcNAcβ1-6Manα1-R and Galβ1-4GlcNAcβ1-6Manα1-R, GalNAcβ1-4GlcNAcβ1-4Manα1-R and Galβ1-4GlcNAcβ1-4Manα1-R, and corresponding sialylated and/or fucosylated analogs of the abovementioned epitopes according to the invention, where R can be for example lactose, any O- or N-glycan or glycolipid core structure, or a spacer that is used for the conjugation of the oligosaccharide to the neoglycoprotein or any other immunogenic carrier by methods known in the art.

In situ generation of LacdiNAc sequences on tissue sections. Tissue controls can be subjected to in situ LacdiNAc synthesis to serve as positive controls in immunohistochemistry or other diagnostic applications. The reaction can be facilitated for example by a mutant β1,4-galactosyltransferase similar to the bovine milk enzyme Y289L mutant described in (Ramakrishnan and Qasba, 2002) and by using reaction conditions essentially similar to ones described in the cited reference. Before the GalNAc transfer reaction, the tissue sections can be incubated with Jack bean β-galactosidase (Glyko, UK) at a concentration of 0.5 U/ml, in 50 mM sodium acetate pH 4.0, at +37° C. overnight, after which the glycosidase reaction solution is washed away from the sections. This will create additional acceptor sites for the GalNAc-transferase.

Use of antibodies in immunodiagnostic applications. The LacdiNAc specific antibodies can be used in immunohistochemistry, immunodiagnostics, and other diagnostic applications according to the standard immunological methods.

Example IV

In Vitro Lysis Assay to Detect Cytolytic Activity of the Antibodies Recognizing lacdiNAc Structures According to the Present Invention.

Model cancer cells comprising lacdiNAc structures on cell surface are harvested to 80% confluent density and washed four times with HBSS (Hank's balanced salt solution). The viability of the cells is determined by trypen blue staining. Approximately 200 000 cells are incubated with antibodies binding the lacdiNAc-structures according to the present invention on the cell surfaces. Rabbit complement is added to one set of cells to a final dilution of 1:5 and the other set of cells is adjusted to same volume with incubation media. The cells are further incubated for 1 h at 37 degree of Celsius. Finally, propium iodide is added to final concentration of 20 micrograms per milliliter and the cells are analyzed for dye uptake. The cells are shown to be lysed by the lacdiNAc binding antibodies but not by non-cancer binding control antibodies. The lacdiNac structures are available for antibody recognition and cytolysis on cell surface.

Example V

Example of α3-Sialyltransferase Reaction:

Molar excess of CMP-NeuNAc (20 micromol) and α3-sialyltransferase (1 U, ST3Gal III, rat liver, Calbiochem) is incubated overnight at 37 degree of Celsius with GalNβ4GlcNAcβ3Lac (5 micromol) in 2.1 ml 50 mM MOPS-NaOH pH 7.4 containing 2 mg/ml BSA. Product NeuNAcα3GalNβ4GlcNAcβ3Galβ4Glc is formed quantitatively and purified by gel filtration HPLC-chromatography. Mass spectrometry and NMR-analysis confirmed the expected structure. MALDI-TOF mass spectrometry in negative linear mode revealed the product peak at m/z 998.36. The products can be optionally N-alkylated or derivatized to an analog of α3-sialylated LacdiNAc. α3-sialylated lacdiNAc is obtained by N-acetylation of GalN to GalNAc by 8 microliters of acetic anhydride in 200 microliters of 1 M NH$_4$HCO$_3$.

Examples of α3-Galactosyltransferase Reactions

Synthesis of Galα3GalNβ4GlcNAcβ3Lac from GalNβ4GlcNAcβ3Lac UDP-Gal (3 micromol), GalNβ4GlcNAcβ3Lac (1.5 micromol), and α3-galactosyltransferase (0.1 U, Calbiochem) is incubated at 37 degrees of Celsius in 500 microliters 100 mM MES buffer pH 7.0 containing 20 mM MgCl$_2$. Product Galα3GalNβ4GlcNAcβ3Galβ4Glc was purified by gel filtration HPLC-chromatography. The reaction was incubated at 37 degrees of Celsius for 4 days. MALDI-TOF mass spectrometry in positive ion mode revealed the expected product peak at m/z 891.2102. The structure of the product is confirmed by NMR-spectrometry.

Example VI

Synthesis of GalNα3GalNβ4GlcNAcβ3Lac from GlcNAcβ3Lac by Two Galactosyltransferases and In Situ Donor Synthesis.

The reaction mixture containing 5 micromol of GlcNAcβ3Lac, 10 mM GalN-1P (Sigma), 20 mM UDP-Glc, 2.5 U galactos-1-phosphate-uridyltransferase, 0.5 U β1-4-galactosyltransferase and 0.5 U α1-3-galactosyltransferase (Calbiochem, Calif., USA) is incubated in 1.0 ml 0.1 M HEPES pH 8.0 containing 5 mM MgCl$_2$ and 5 mM β-mercaptoethanol. The reaction was incubated at 37 degrees of Celsius for 4 days. MALDI-TOF analysis of the reaction products in positive ion mode revealed major product peak at m/z 890.2349. The structure of the product is confirmed by NMR-spectrometry.

REFERENCES

Arap, W., Pasqualini, R. and Ruoslahti, E. (1998) Science 279, 3234.

Bergwerff, A. A., van Kuik, J. A., Schiphorst, W. E. C. M., Koeleman, C. A. M., van den Eijnden, D. H., Kamerling, J. P., and Vhiegenthart, J. F. G. (1993) FEBS Lett. 334, 133-138

Dell, A., Morris, H. R., Easton, R. L., Panico, M., Patankar, M., Oehringer, S., Koistinen, R., Koistinen, H., Seppälä, M. and Clark, G. F. (1995) J. Biol. Chem. 270, 24116-24126.

Do, K-Y, Do, S-I and Cummings, R. D. (1997) Glycobiology 7, 183-194.

Grinnel, B. W., Hermann, R. B. and Yan, S. B. (1994) Glycobiology 4, 221-225.

Harvey, D. J., et al. (1993) Rapid Commun. Mass Spectrom. 7(7):614-9.

Jain, R K., Piskortz, C. F., Huang, B-G, Locke, R. D., Han, H-L, Koenig, A., Varki, A. and Matta, K. L. (1998) Glycobiology 8, 707-717.

Jaques, A. J., Opdennakker, G., Rademacher, R. A., Dwek, R. A. and Zamze, S. E. (1996) Biochem. J. 316, 427-437.

Koivunen E., Arap W., Valtanen H., Rainisalo A., Medina O P., Heilddla P., Kantor C., Gahmberg C. G., Salo T., Konttinen Y. T., Sorsa T., Ruoslahti E. and Pasqualini R. (1999) Nature Biotechnology 17(8):768-74.

Manzella, S. M., Dharmesh, S. M., Cohick, C. B., Soares, M. J. and Baenziger, J. U. (1997) J. Biol. Chem. 272, 4775-4782.

Manzi, A. E., et al. (2000) Glycobiology 10(7):669-89

Ramakrishnan, B., and Qasba P. K. (2002) J. Biol. Chem. 277, 20833-39.

Rudd, P. M., Mattu, T. S., Masure, S., Bratt, T., van den Steen, P. E., Wormald, M. R., Kuester, B., Harvey, D. J., Borre-

TABLE 1

| assignment | MMP-9 glycans, peak 23.10 m/z | z | m (observed) | m (calculated) | abundance % (of total)* | LacDiNac % | corresponding signal in MALDI analysis (FIG. 1A)** |
|---|---|---|---|---|---|---|---|
| Hex5HexNac4Fuc1 | 1070.201 | 4 | 4276.804 | 4276.812 | 10.1 | | |
| Hex4HexNac5Fuc1 | 1080.498 | 4 | 4317.992 | 4317.838 | 4.8 | 4.8 | |
| Hex5HexNac4Fuc2 | 1106.763 | 4 | 4423.052 | 4422.87 | 13.4 | | 1956.01 |
| Hex4HexNac5Fuc2 | 1117.036 | 4 | 4464.144 | 4463.896 | 7.8 | 7.8 | 1996.64 |
| Hex5HexNac4Fuc3 | 1143.247 | 4 | 4568.988 | 4568.928 | 21.2 | | 2101.96 |
| Hex4HexNac5Fuc3 | 1153.518 | 4 | 4610.072 | 4609.954 | 8.1 | 8.1 | 2143.07 |
| | | | | | 65.5 | 20.7 | |

| assignment | MMP-9 glycans, peak 24.30 m/z | z | m | | abundance % (of total)* | LacDiNac % | |
|---|---|---|---|---|---|---|---|
| Hex5HexNac4SA1 | 1106.697 | 4 | 4422.788 | 4421.849 | 2.9 | | |
| Hex5HexNac4Fuc1SA1 | 1143.008 | 4 | 4568.032 | 4567.907 | 10.6 | | |
| Hex4HexNac5Fuc1SA1 | 1153.318 | 4 | 4609.272 | 4608.964 | 3.1 | 3.1 | |
| Hex5HexNac4Fuc2SA1 | 1179.540 | 4 | 4714.16 | 4713.965 | 13.7 | | 2247.27 |
| Hex4HexNac5Fuc2SA1 | 1189.780 | 4 | 4785.12 | 4754.992 | 4.1 | 4.1 | 2288.22 |
| | | | | | 34.5 | 7.2 | |
| total abundance (%) | | | | | 100.0 | 27.9 | |

*Quantification based on LC/MS analysis
**Analysed as [M + Na]$^{+Ion}$ gard, N., Van Damme, J., Dwek, R. A. and Obdenakker, G. (1999) Biochemistry 38, 13937-13950.
Nyame, K, Leppänen A. M., Bogitsh, B. J., and Cummings, R. D. (2000) Exp. Parasitol. 96, 202-212
Nyman, T. A., et al. (1998) Eur. J. Biochem. 253(2):485-93
Ohkura, T., Hara-Kuge, S., and Yamashita, K (2001) Glyco XVI International Symposium on Glycoconjugates August 19-24, The Hague, The Netherlands, Abstract C20.3. abstract book page 79.
Packer, N. H., et al. (1998) Glycoconj. J. 15(8):737-747
Papac, D. I., et al (1996) Anal. Chem. 68(18):3215-23
Saarinen, J., Welgus, H. G., Flizar, C. A., Kaikdnen N. and Helin J. (1999) Eur. J. Biochem. 259, 829-840.
van den Eijnden, D. H., Bakker, H., Neeleman, A. P., van den Nieuwenhof, I. M. and van Die I. (1997) Biochem Soc. Trans. 25, 887-893.
Verostek, M. F., et al. (2000) Anal. Biochem. 278:111-122.
Yang, Y., V. Hayden, T, Man, S. and Rice, K. G. (2000) Glycobiology 10, 1341-1345.

What is claimed:

1. A method for diagnosing larynx cancer in a larynx tissue sample from a patient suspected of having larynx cancer comprising determining the presence in said larynx tissue sample of an oligosaccharide sequence according to Formula $$(Sac1)_x GalNAc\beta 4(Fuc\alpha 3)_y GlcNAc \quad (I)$$

wherein x and y are each independently 0 or 1 and Sac1 is NeuNAcα3 or NeuNAcα6,
and wherein the determination comprises
(a) contacting said larynx tissue sample with an antibody to said oligosaccharide sequence, and
determining the presence of a combination of said antibody bound to said oligosaccharide sequence, the presence of said oligosaccharide sequence being an indication of the presence of larynx cancer in said larynx tissue sample, or
(b) releasing the oligosaccharide structures from said larynx tissue sample by enzymatic or chemical methods to form a fraction containing free oligosaccharide structures or conjugates from said larynx tissue sample, and determining the presence of said oligosaccharide sequence in said fraction, the presence of said oligosaccharide sequence in said fraction being an indication of the presence of larynx cancer in said larynx tissue sample.

2. The method according to claim 1, wherein said antibody is specific to oligosaccharide sequence GalNAcβ4GlcNAc.

3. The method according to claim 1, wherein said antibody is specific to the oligosaccharide sequence according to Formula I.

4. A method for diagnosing larynx cancer in a larynx tissue sample comprising determining the presence in said larynx tissue sample of an oligosaccharide sequence according to Formula $$(Sac1)_x GalNAc\beta 4(Fuc\alpha 3)_y GlcNAc \quad (I)$$

wherein x and y are each independently 0 or 1 and Sac1 is NeuNAcα3 or NeuNAcα6,
and wherein the determination comprises
(a) contacting said larynx tissue sample with an antibody to said oligosaccharide sequence, and
determining the presence of a combination of said antibody bound to said larynx tissue sample, and
(b) contacting a control larynx tissue sample of corresponding healthy tissue with said antibody, and determining the presence of a combination of said antibody bound to said control larynx tissue sample, wherein a higher presence of said oligosaccharide sequence in said larynx tissue sample compared to said control larynx tissue sample is indicative of larynx cancer in said larynx tissue sample; or
(c) releasing the oligosaccharide structures from said larynx tissue sample by enzymatic or chemical methods to form a fraction containing free oligosaccharide structures or conjugates from said larynx tissue sample, and determining the presence of said oligosaccharide sequence in said fraction; and
(d) releasing the oligosaccharide structures from said control larynx tissue sample by enzymatic or chemical methods to form a fraction containing free oligosaccharide structures or conjugates from said control larynx tissue sample, and determining the presence of said oligosaccharide sequence in said fraction, wherein a higher presence of said oligosaccharide sequence in the fraction obtained from said larynx tissue sample compared to the fraction obtained from said control larynx tissue sample is indicative of the presence of larynx cancer in said sample.

5. The method according to claim 4, wherein said antibody is specific to the oligosaccharide sequence according to Formula I.

6. The method according to claim 4, wherein said antibody is specific to oligosaccharide sequence GalNAcβ4GlcNAc.

7. The method according to claim 1, wherein the detected oligosaccharide sequence is on cell or tissue surface.

8. The method according to claim 4, wherein the detected oligosaccharide sequence is on cell or tissue surface.

9. The method according to claim 1, wherein in Formula (I), y is 1 only when x is 1.

10. The method according to claim 4, wherein the presence of said oligosaccharide sequence is determined in step c) or d) by NMR-spectroscopy, mass spectrometry or glycosidase degradation methods.

11. The method according to claim 4, wherein the larynx tissue sample is taken from a patient suspected to suffer from larynx cancer.

12. The method according to claim 4, wherein the larynx tissue sample is a tumor sample or a sample of larynx tissue that is suspected to be cancerous.

13. A method for screening tumor or cancer tissue samples for the presence of an oligosaccharide according to Formula $$(Sac1)_x GalNAc\beta 4(Fuc\alpha 3)_y GlcNAc \quad (I)$$

wherein x and y are each independently 0 or 1 and Sac1 is NeuNAcα3 or NeuNAcα6,
and wherein the determination comprises
(a) contacting said tissue sample with an antibody to said oligosaccharide sequence, and
determining the presence of a combination of said antibody bound to said tissue sample, and
(b) contacting a control sample of corresponding healthy tissue with said antibody, determining the presence of a combination of said antibody bound to said control sample, and comparing the level of said oligosaccharide sequence in said tissue sample to that in said control sample; or
(c) releasing the oligosaccharide structures from said tissue sample by enzymatic or chemical methods to form a fraction containing free oligosaccharide structures or conjugates from said tissue sample, and determining the presence of said oligosaccharide sequence in said fraction; and
(d) releasing the oligosaccharide structures from said control sample by enzymatic or chemical methods to form a fraction containing free oligosaccharide structures or conjugates from said control sample, determining the presence of said oligosaccharide sequence in said fraction, and comparing the level of said oligosaccharide sequence in the fraction obtained from said tissue sample to that in the fraction obtained from said control sample.

14. The method according to claim 13, wherein said tumor or cancer tissue is from leukemia, melanoma or larynx cancer.

15. A method for analysing a putative cancer sample comprising determining the presence in said sample of an oligosaccharide sequence according to Formula

(I)

wherein x and y are each independently 0 or 1 and Sac1 is NeuNAcα3 or NeuNAcα6, wherein the determination comprises (a) contacting said putative cancer sample with an antibody binding to said oligosaccharide sequence, and determining the presence of a combination of said antibody and said sample, the presence of said combination being an indication of the presence of said oligosaccharide in said sample, or (b) releasing the oligosaccharide structures of said putative cancer sample by enzymatic or chemical methods to form a fraction containing free oligosaccharide structures or conjugates from said sample, and determining the presence of said oligosaccharide sequence in said fraction.

16. The method according to claim 15, wherein said putative cancer sample is from leukemia, melanoma or larynx cancer.

17. The method according to claim 15, wherein the putative cancer sample is from a human or animal patient suspected to have cancer.

18. The method according to claim 15, wherein the method comprises a further step of purification, detection or quantitation of an antibody binding to the oligosaccharide sequence according to Formula I from the serum of a patient, when the presence of an oligosaccharide sequence according to Formula I is detected in said sample.

19. The method according to the claim 13, wherein the method comprises a further step of purification, detection or quantitation of an antibody binding to the oligosaccharide sequence according to Formula I from the serum of a patient, when the presence of an oligosaccharide sequence according to Formula I is detected in said sample.

20. The method according to the claim 15, wherein step (a) is performed as an in vitro cytolysis assay of cancer cells with antibodies binding to the oligosaccharide sequence according to Formula I.

* * * * *